(12) United States Patent
Fujiyama et al.

(10) Patent No.: US 10,768,102 B2
(45) Date of Patent: Sep. 8, 2020

(54) MOISTURE CONTENT OBSERVATION DEVICE, MOISTURE CONTENT OBSERVATION METHOD, AND CULTIVATING DEVICE

(71) Applicant: PANASONIC INTELLECTUAL PROPERTY MANAGEMENT CO., LTD., Osaka (JP)

(72) Inventors: Takeshi Fujiyama, Fukuoka (JP); Yuuji Terashima, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 187 days.

(21) Appl. No.: 16/065,892

(22) PCT Filed: Feb. 20, 2017

(86) PCT No.: PCT/JP2017/006101
§ 371 (c)(1),
(2) Date: Jun. 25, 2018

(87) PCT Pub. No.: WO2017/145980
PCT Pub. Date: Aug. 31, 2017

(65) Prior Publication Data
US 2018/0372624 A1    Dec. 27, 2018

(30) Foreign Application Priority Data
Feb. 26, 2016   (JP) .................................. 2016-036404

(51) Int. Cl.
*G01N 21/3554*    (2014.01)
*A01G 7/00*    (2006.01)
(Continued)

(52) U.S. Cl.
CPC ........... *G01N 21/3554* (2013.01); *A01G 7/00* (2013.01); *A01G 27/00* (2013.01);
(Continued)

(58) Field of Classification Search
CPC .................................................. G01N 21/3554
See application file for complete search history.

(56) References Cited

U.S. PATENT DOCUMENTS 5,001,346 A *   3/1991   Barkhoudarian ....... G01M 3/38
                                                                   250/330
5,179,422 A *   1/1993   Peterson ................. G01N 21/94
                                                                  250/559.41
(Continued)

FOREIGN PATENT DOCUMENTS

EP          2405258 A2     1/2012
JP        2001-272373     10/2001

OTHER PUBLICATIONS

The Extended European Search Report dated Nov. 27, 2018 for the related European Patent Application No. 17756418.4.
(Continued)

*Primary Examiner* — Edwin C Gunberg
(74) *Attorney, Agent, or Firm* — Greenblum & Bernstein, P.L.C.

(57) ABSTRACT

A threshold level setter/water content index detector calculates an $\Sigma \ Ln \ (I_{905}/I_{1550})$ which is a total sum of the reflection intensity ratio as a water content index of one leaf. A controller displays a graph representing the time-transition of the water content contained in the leaf of the plant from the start to the end of the measurement period on a UI screen of monitor 50. The controller fixedly determines and sets, as a leaf, a set of reflection positions where the water content for each reflection position which is calculated at the start of the measurement period exceeds a threshold level. When viewed from first beam source and second beam source, white reference substrate which covers a back surface of the leaf of the plant is disposed on the leaf of the plant.

5 Claims, 32 Drawing Sheets

(51) Int. Cl.
  *A01G 27/00* (2006.01)
  *G01N 33/00* (2006.01)
  *G01N 21/359* (2014.01)
  *G01N 21/31* (2006.01)
  *G01N 21/84* (2006.01)
  *G01N 21/27* (2006.01)

(52) U.S. Cl.
  CPC ......... *G01N 33/0098* (2013.01); *G01N 21/27* (2013.01); *G01N 21/3151* (2013.01); *G01N 21/359* (2013.01); *G01N 2021/8466* (2013.01)

(56) References Cited

U.S. PATENT DOCUMENTS

| | | | |
|---|---|---|---|
| 10,309,896 B2* | 6/2019 | Fujiyama | G01N 21/359 |
| 10,613,024 B2* | 4/2020 | Fujiyama | G01N 21/3151 |
| 2017/0115210 A1 | 4/2017 | Fujiyama et al. | |

OTHER PUBLICATIONS

Gaulton R et al: "The potential of dual-wavelength laser scanning for estimating vegetation moisture content", Remote Sensing of Environment, Elsevier, XX, vol. 132, Jan. 31, 2013 (Jan. 31, 2013), pp. 32-39, XP028522997.

International Search Report (ISR) issued in International Patent Application No. PCT/JP2017/006101, dated May 9, 2017.

U.S. Appl. No. 15/525,431 to Takeshi Fujiyama et al., filed May 9, 2017.

U.S. Appl. No. 15/779,759 to Takeshi Fujiyama et al., filed May 29, 2018.

U.S. Appl. No. 16/066,216 to Takeshi Fujiyama et al., filed Jun. 26, 2018.

U.S. Appl. No. 16/074,285 to Takeshi Fujiyama et al., filed Jul. 31, 2018.

* cited by examiner

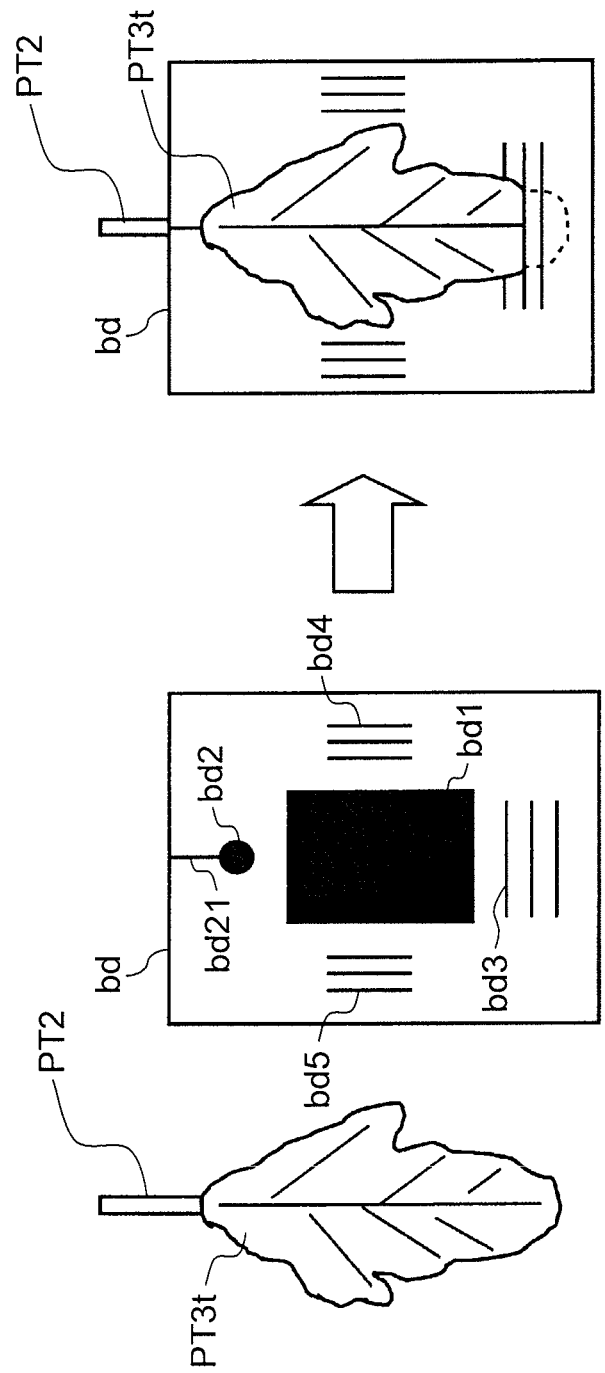

BEFORE POSITIONAL DEVIATION

AFTER POSITIONAL DEVIATION

FIG. 23

| TIME | ELAPSED TIME (MINUTE) | STANDARDIZED PIXEL AVERAGE WATER CONTENT INDEX | |
| --- | --- | --- | --- |
| | | BEFORE CORRECTION | AFTER CORRECTION |
| ⋮ | 15950 | 0.6879 | 0.6879 |
| | 15980 | 0.6586 | 0.6586 |
| | 16010 | 0.6639 | 0.6639 |
| | 16040 | 0.6674 | 0.6674 |
| | 16070 | 0.6650 | 0.6650 |
| | 16100 | 0.6593 | 0.6593 |
| | 16130 | 0.6425 | 0.6425 |
| | 16160 | 0.6503 | 0.6503 |
| | 16190 | 0.6530 | 0.6530 |
| | 16220 | 0.6416 | 0.6416 |
| 17:10 | 16250 | CORRECTION OF DEVIATION ↓ | |
| | 16280 | | |
| 18:40 | 16310 | 0.8785 | 0.6416 |
| | 16340 | 0.8694 | 0.6350 |
| | 16370 | 0.8444 | 0.6167 |
| | 16400 | 0.8515 | 0.6218 |
| ⋮ | 16430 | 0.8524 | 0.6225 |
| | 16460 | 0.8584 | 0.6269 |
| | 16490 | 0.8647 | 0.6315 |
| | 16520 | 0.8601 | 0.6281 |
| | 16550 | 0.8400 | 0.6135 |

FIG. 27

| REFLECTION INTENSITY RATIO<br>Ln (I₉₀₅/I₁₅₅₀) | INTENSITY RATIO CALCULATION<br>I₉₀₅/I₁₅₅₀ |
|---|---|
| < 0.3 | < 1.349 |
| 0.3 ~ 0.4 | 1.349 ~ 1.492 |
| 0.4 ~ 0.5 | 1.492 ~ 1.649 |
| 0.5 ~ 0.55 | 1.649 ~ 1.733 |
| 0.55 ~ 0.6 | 1.733 ~ 1.822 |
| 0.6 ~ 0.75 | 1.822 ~ 2.117 |
| 0.75 < | 2.117 < |

| 0.120811 | 0.149614 | 0.137343 | 0.114148 | 0.076093 | 0.011674 | -0.01163 | -0.05523 | -0.03757 |
|---|---|---|---|---|---|---|---|---|
| 0.125248 | 0.172965 | 0.15948 | 0.126022 | 0.089612 | 0.01949 | 0.011873 | -0.03391 | -0.01574 |
| 0.148199 | 0.199904 | 0.17691 | 0.133531 | 0.111832 | 0.044927 | 0.052822 | 0.008977 | 0.022246 |
| 0.194251 | 0.227869 | 0.198172 | 0.156277 | 0.154876 | 0.102169 | 0.119502 | 0.074724 | 0.075352 |
| 0.247982 | 0.262199 | 0.239978 | 0.215673 | 0.229191 | 0.192649 | 0.214218 | 0.156125 | 0.136483 |
| 0.276739 | 0.287792 | 0.295587 | 0.296691 | 0.326487 | 0.302588 | 0.32026 | 0.237615 | 0.191142 |
| 0.254583 | 0.278097 | 0.324702 | 0.364308 | 0.412217 | 0.409069 | 0.410649 | 0.302116 | 0.230093 |
| 0.199545 | 0.234741 | 0.302685 | 0.394193 | 0.454575 | 0.470076 | 0.45354 | 0.329293 | 0.250862 |
| 0.15815 | 0.197794 | 0.272265 | 0.394631 | 0.456677 | 0.485935 | 0.461736 | 0.330715 | 0.251775 |
| 0.161212 | 0.206592 | 0.282619 | 0.409233 | 0.458335 | 0.474655 | 0.45055 | 0.321021 | 0.242244 |
| 0.204409 | 0.269788 | 0.342894 | 0.450824 | 0.474401 | 0.460903 | 0.427522 | 0.301546 | 0.219295 |
| 0.256744 | 0.348575 | 0.412386 | 0.497288 | 0.490421 | 0.435941 | 0.390092 | 0.270651 | 0.186504 |
| 0.292105 | 0.406767 | 0.453507 | 0.506656 | 0.485508 | 0.402278 | 0.333888 | 0.226336 | 0.146093 |
| 0.295668 | 0.42312 | 0.463995 | 0.481857 | 0.449536 | 0.350517 | 0.26229 | 0.180838 | 0.103744 |
| 0.265075 | 0.398231 | 0.445507 | 0.423915 | 0.374375 | 0.281667 | 0.181745 | 0.129034 | 0.062051 |
| 0.214678 | 0.344539 | 0.393603 | 0.348569 | 0.277132 | 0.203423 | 0.103611 | 0.077881 | 0.01823 |
| 0.169447 | 0.275706 | 0.315009 | 0.261335 | 0.175947 | 0.124205 | 0.031069 | 0.018942 | -0.01898 |
| 0.141768 | 0.214221 | 0.230803 | 0.178572 | 0.093177 | 0.062106 | -0.02083 | -0.01928 | -0.02509 |
| 0.1265 | 0.162033 | 0.159463 | 0.116279 | 0.041841 | 0.020169 | -0.03136 | -0.01489 | 0.004509 |
| 0.094079 | 0.112334 | 0.093124 | 0.074864 | 0.023198 | 0.023857 | -0.00217 | 0.025928 | 0.059011 |
| 0.043646 | 0.055988 | 0.032287 | 0.048581 | 0.024701 | 0.045375 | 0.056402 | 0.089247 | 0.11396 |

ARE

A
B

MOISTURE CONTENT OBSERVATION DEVICE, MOISTURE CONTENT OBSERVATION METHOD, AND CULTIVATING DEVICE

TECHNICAL FIELD

The present disclosure relates to a device for observing water content contained in a plant, a method for observing water content, and a cultivation device.

BACKGROUND ART

There is a potential difference inside and outside of a cell in a normal plant and electromotive force is generated. It is possible to describe a mechanism which generates such electromotive force based on, for example, an electrophysiological model of an axial organ of a higher plant.

In particular, various methods are suggested in which a state of a root of the plant (for example, water stress) is examined non-destructively utilizing electromotive force between the root and soil.

As a prior technique in which water stress in a plant is measured utilizing the method described above, for example, Patent Document 1 is known. In Patent Document 1, connecting a first nonpolarizable electrode to the plant, connecting a second nonpolarizable electrode to soil in which the plant is planted, providing a potentiometer between the two nonpolarizable electrodes, and being able to measure water stress which is received by the plant by measuring electromotive force between both nonpolarizable electrodes using the potentiometer.

In order to accurately evaluate a time-transition of the amount of applied water stress in the leaf of the plant, it is important that specification of an initial shape of the leaf of the plant that is a measurement target is a criterion, and the water content of the leaf is observed based on the specified shape. In farmers cultivating the plant (for example, vegetables such as tomatoes), in order to improve the value of tomato (that is, the unit price), for example, it is conceivable to improve the sugar content of tomatoes. Here, the kind of irrigation to be performed and the timing of the irrigation for increasing the sugar content is mainly attributable to artificial arrangements such as farmer's past experience and intuition.

In general, increasing the sugar content of fruits such as tomatoes leads to an improvement in quality and a rise in unit prices, but has a strong aspect that since growing such fruits is not easy, yield is decreased and thereby the production amount is also decreased. In other words, there is a trade-off relationship between high performance of fruits and the yield. For this reason, in the future, it is expected to increase the productivity by improving the yield.

An object of the present disclosure is to quantitatively and time-serially suggest a change of a water content contained in a plant and accurately capture the change of the water content from an initial stage with respect to the extent of water stress applied to the plant.

CITATION LIST

Patent Literature

PTL 1; Japanese Patent Unexamined Publication No. 2001-272373

SUMMARY OF THE INVENTION

A device for observing water content in a plant of the present disclosure includes a first light source which radiates a near infrared laser reference beam of a first wavelength having a characteristic in which light tends not to be absorbed in water while sequentially scanning toward a plant; a second light source which radiates a near infrared laser measuring beam of a second wavelength having a characteristic in which light tends to be absorbed in water while sequentially scanning toward the plant; an output unit that outputs an invisible light image indicating presence or absence of water contained in the plant; a water content calculation unit that repeatedly calculates the water content contained in each pixel area constituting the invisible light image based on reflection light of the near infrared laser reference beam and reflection light of the near infrared laser measuring beam, in a certain measurement period; and a controller that displays a time-transition of the water content in the pixel area from start to end of the measurement period, which is calculated by the water content calculation unit on a display unit, in which the controller fixedly determines a set of pixel areas in which the water content calculated by the water content calculation unit exceeds a threshold level at the start of the measurement period, out of all pixel areas constituting the invisible light image, as an observation target portion of the plant.

The cultivation device of the present disclosure is provided with the device for observing water content, and a cultivation controller that irrigates the plant with a predetermined amount of water based on the time-transition of the water content calculated by the water content calculation unit in a certain period of the measurement periods.

In addition, a method for observing water content in a device for observing water content in a plant of the present disclosure, the method includes radiating a near infrared laser reference beam of a first wavelength having a characteristic in which light tends not to be absorbed in water while sequentially scanning toward a plant, by a first light source; radiating a near infrared laser measuring beam of a second wavelength having a characteristic in which light tends to be absorbed in water while sequentially scanning toward the plant, by a second light source; outputting an invisible light image indicating presence or absence of water contained in the plant; repeatedly calculating the water content contained in each pixel area constituting the invisible light image based on reflection light of the near infrared laser reference beam and reflection light of the near infrared laser measuring beam, in a certain measurement period; and displaying a time-transition of the calculated water content in the pixel area from start to end of the measurement period, in which an observation target portion of the plant is fixedly determined as a set of pixel areas in which the water content calculated at the start of the measurement period exceeds a threshold level, out of all pixel areas constituting the invisible light image.

According to the present disclosure, it is possible to quantitatively and time-serially suggest the change of the water content contained in the plant and accurately capture the change of the water content from the initial stage of the application of the water stress with respect to the plant.

BRIEF DESCRIPTION OF DRAWINGS

FIG. 11 is a diagram which describes an example of attachment of the leaf on a white reference substrate.

FIG. 23 is a diagram illustrating a table indicating an example of the standardized pixel average water content index before and after positional deviation correction in time series.

FIG. 27 is a diagram illustrating a table that indicates tone color corresponding to reflection intensity ratio.

FIG. 28 is a diagram illustrating a table that indicates the reflection intensity ratio in a portion of a frame image including a pixel space occupied by the leaf.

DESCRIPTION OF EMBODIMENTS

Hereinafter, embodiments in which a device for observing water content, a cultivation device, and a method for observing water content according to the present disclosure are specifically described are described in detail with reference to the drawings as appropriate. However, detailed description may be omitted as necessary. For example, detailed description of already well-known matter and overlapping description with respect to substantially the same configuration may be omitted. This is because the following description is prevented from unnecessarily becoming redundant, and a process of the inventor is easily set. Note that, drawings and the following description are provided by the inventor for sufficient understanding of the present disclosure, and thereby, the present disclosure is not intended to be limited to a subject described in the range of the claims.

First Embodiment

Figure 1:
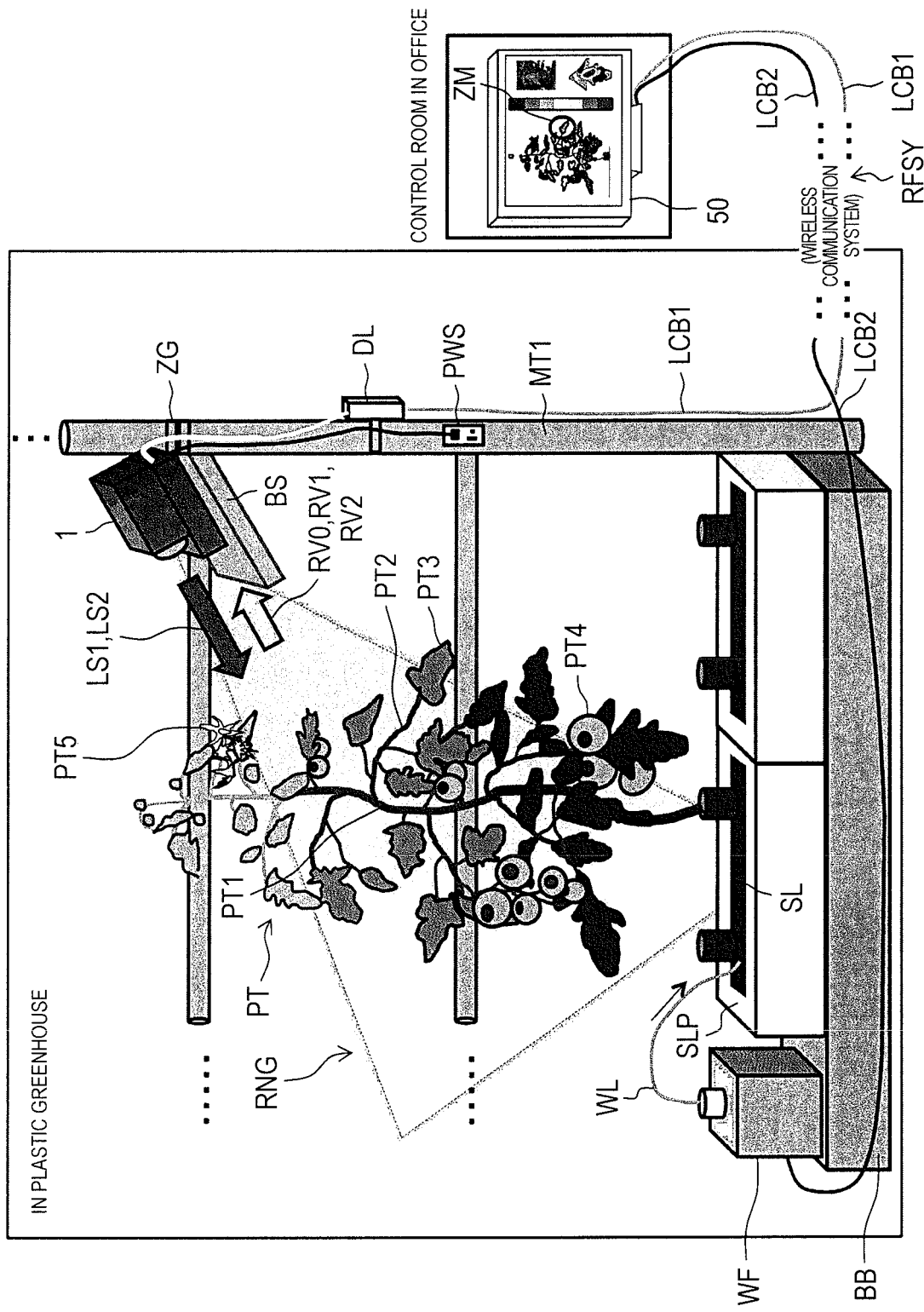
FIG. 1 is a conceptual explanatory diagram illustrating an example of usage circumstances of a plant detection camera in a first embodiment.

As an example of the device for observing water content of the present embodiment, description will be given by exemplifying plant detection camera 1 as illustrated in FIG. 1. In addition, the cultivation device of the present embodiment has a configuration of including plant detection camera 1 as illustrated in FIG. 1, fertilizer or water supply device WF as an example of a cultivation controller that supplies a fertilizer (for example, a liquid fertilizer) or irrigates the plant with a predetermined amount of the water content, and monitor 50 that displays (user interface) screen 60 (refer to FIG. 16) or the like. Further, the present disclosure can realize a method for observing water content for executing each process performed by plant detection camera 1. Plant detection camera 1 of the present embodiment is able to detect a distribution state of presence or absence of water content of the leaf or the part of the plant.

Hereinafter, the leaf is exemplified as a target portion of the plant, but the target portion of the plant is not limited to the leaf, and other parts such as a fruit, a stem, a flower, and a root may be used.

Here, an observation target of plant detection camera 1 of the present embodiment is the plant, and description is made by exemplifying a fruit vegetable that is given as a more specific example. Since sugar content of a fruit of a tomato is increased in growth of fruit vegetables such as, for example, the tomato, it is known that it is necessary for water or fertilizer to be in an insufficient state to some extent and not a state in which water or fertilizer is sufficiently supplied as a result of water or fertilizer of a root or a leaf being digested by a suitable amount in photosynthesis. For example, if sufficient water is supplied to the leaf, the leaf has a flat shape in a sound state. Meanwhile, when water of the leaf is equivalently insufficient, the shape of the leaf is bent. Meanwhile, when fertilizer in the soil is equivalently insufficient, a condition is generated of the leaf turning yellow and the like.

In the present embodiment below, an example is described in which plant detection camera 1 radiates laser beams of a plurality of types which are different in wavelength on the plant (for example, leaf), and detects water content of the leaf based on an intensity ratio of respective diffuse reflection light that are reflected on irradiation positions (in other words, a reflection position of the leaf irradiated with the laser beam or an area indicating each pixel constituting a visible light captured image obtained by imaging the leaf) of the leaf.

Outline of Plant Detection Camera

FIG. 1 is a conceptual explanatory diagram illustrating an example of usage circumstances of plant detection camera 1 in a first embodiment. Plant detection camera 1 is installed at a fixed point within a greenhouse in which, for example, fruit vegetables such as the tomato are planted. In detail, for example, plant detection camera 1 is installed on base BS that is fixed to mounting jig ZG which is attached so as to interpose support column MT1 with a cylindrical shape extending in a vertical direction from the ground. Plant detection camera 1 operates by power to be supplied from power source switch PWS that is attached to support column MT1, and radiates reference beam LS1 and measuring beam LS2 that are a plurality of types of laser beams which have different wavelengths toward plant PT that is the observation target across irradiation range RNG.

Plant PT is, for example, a fruit vegetable plant such as the tomato, a root of plant PT which grows from soil SL that is filled in soil pot SLP which is installed on base BB, and plant PT has each of stem PT1, stalk PT2, leaf PT3, fruit PT4, and flower PT5. Fertilizer or water supply device WF is installed on base BB. Fertilizer or water supply device WF supplies water to soil pot SLP via, for example, cable WL according to an instruction from wireless communication system RFSY that is connected via local area network (LAN) cable LCB2. Thereby, since water is supplied to soil SL, the root of plant PT absorbs water, and transmits water to each part within plant PT (that is, stem PT1, stalk PT2, leaf PT3, fruit PT4, and flower PT5).

In addition, plant detection camera 1 receives diffuse reflection light RV1 and RV2 that are reflected on an irradiation position of plant PT which is radiated by reference beam LS1 and measuring beam LS2, and furthermore, receives ambient light RV0. As will be described later, plant detection camera 1 has a normal camera function, and is able to image an image (that is, visible light image of plant PT within the greenhouse indicated in FIG. 1) within a default angle of view due to ambient light RV0 entering. Plant detection camera 1 outputs output data which includes various detection results (refer to description below) or image data to data logger DL based on diffuse reflection light RV1 and RV2.

Data logger DL transmits output data from plant detection camera 1 to management personal computer (PC) of a control room within an office at a position geographically separated from the greenhouse via LAN cable LCB1 and wireless communication system RFSY. Wireless communication system RFSY is not particularly limited in communication specification, but controls communication between data logger DL within the greenhouse and management PC within the control room in the office, and furthermore transmits an instruction from management PC which relates to supply of water or fertilizer of soil pot SLP to fertilizer or water supply device WF.

Monitor 50 is connected to management PC within the control room in the office, and management PC displays output data of plant detection camera 1 that is transmitted from data logger DL on monitor 50. In FIG. 1, for example, monitor 50 displays the entirety of plant PT that is the observation target and a distribution state which relates to presence or absence of water in the entirety of plant PT. In addition, monitor 50 generates and is able to comparatively display an enlargement distribution state of a specific designated location out of the entirety of plant PT (that is, designated location ZM that is specified by a zoom operation of an observer who uses management PC) and image data corresponding to the designated location of the enlargement distribution state. Further, monitor 50, which is an example of the display unit, displays UI screen 60 including screen for monitoring water content in leaf Gm1 (refer to FIG. 16) described later.

Plant detection camera 1 has a configuration which includes visible light camera VSC and invisible light sensor NVSS. Visible light camera VSC as an example of an acquiring unit images plant PT within the greenhouse using ambient light RV0 with respect to invisible light that has a predetermined wavelength (for example, 0.4 to 0.7 μm) in the same manner as, for example, existing monitoring camera. Image data of the plant that is imaged by visible light camera VSC refers to "visible light camera image data".

Invisible light sensor NVSS incidents reference beam LS1 and measuring beam LS2 which is invisible light (for example, infrared beam) that has a plurality of types of wavelengths (refer to description below) with respect to the same plant PT as visible light camera VSC. Invisible light sensor NVSS detects presence or absence of water at the irradiation position (in other words, an area indicating individual pixels constituting a captured image of the leaf irradiated with reference beam LS1 and measuring beam LS2, or reflection position where a laser beam is reflected.) of plant PT which is the observation target using the intensity ratio of diffuse reflection light RV1 and RV2 that are reflected on the irradiation position of plant PT which is radiated by reference beam LS1 and measuring beam LS2.

In addition, in visible light camera image data that is imaged by visible light camera VSC, plant detection camera 1 generates and outputs output image data (hereinafter referred to as "detection result image data") which is equivalent to the detection result of water of invisible light sensor NVSS or display data that composites information which relates to detection result image data. Display data is not limited to image data in which detection result image data and visible light camera image data are composited, and for example, may be image data that is generated such that detection result image data and visible light camera image data are able to be compared. An output destination of the display data from plant detection camera 1 is an externally connected device that is connected to plant detection camera 1 via, for example, a network, and is data logger DL or communication terminal MT (refer to FIG. 2). The network may be a wired network (for example, intranet or internet), and may be a wireless network (for example, wireless LAN).

Description of Each Part of Plant Detection Camera

Figure 2:
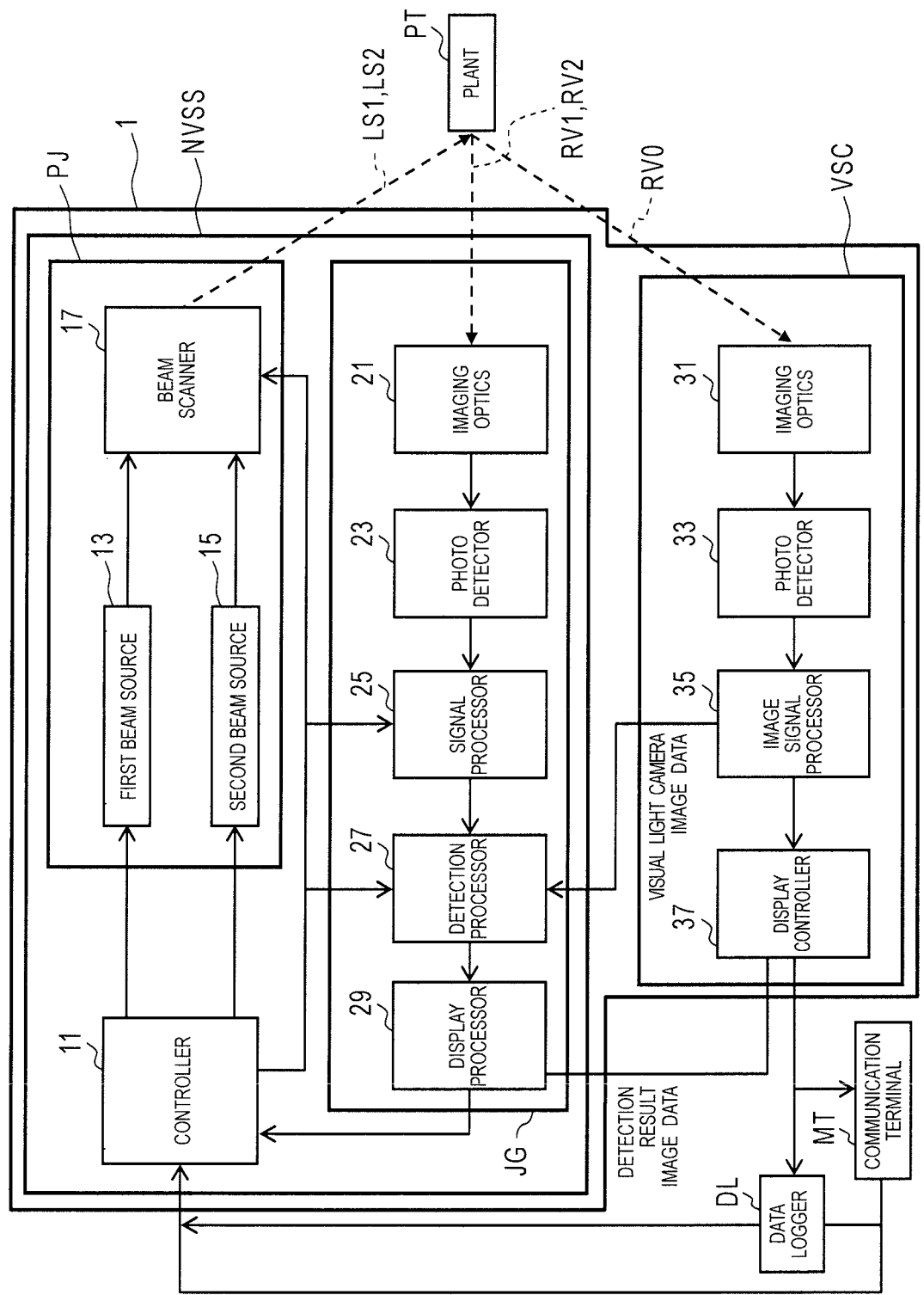
FIG. 2 is a block diagram illustrating in detail an example of an internal configuration of the plant detection camera.

FIG. 2 is a block diagram illustrating in detail an example of an internal configuration of plant detection camera 1. Plant detection camera 1 which is illustrated in FIG. 2 has a configuration which includes invisible light sensor NVSS and visible light camera VSC. Invisible light sensor NVSS has a configuration which includes controller 11, beam output PJ, and determiner JG. Beam output PJ has first beam source 13, second beam source 15, and beam scanner 17. Determiner JG has imaging optics 21, photo detector 23, signal processor 25, detection processor 27, and display processor 29. Visible light camera VSC has imaging optics 31, photo detector 33, image signal processor 35, and display controller 37. Communication terminal MT is portable by a user (for example, observer of growth of plant PT of fruit vegetable plant such as the tomato, hereinafter the same).

In the description of each part of plant detection camera 1, controller 11, invisible light sensor NVSS, and visible light camera VSC are described in order.

Controller 11 is configured using, for example, a central processor (CPU), a microprocessor (MPU), or a digital signal processor (DSP), (and also configured using, for example, a program memory and a work memory,) and performs a signal process for totally controlling an operation control of each part of visible light camera VSC and invisible light sensor NVSS, an input and output process of data within other parts, a computing process of data, and a storage process of data. In addition, controller 11 includes timing controller 11a described later (refer to FIG. 3).

Controller 11 sets detection threshold level M of plant PT which is the detection target of invisible light sensor NVSS to detection processor 27 described later. Details of the operation of controller 11 will be described later with reference to FIG. 4.

Timing controller 11a controls output of first beam source 13 and second beam source 15 in beam output PJ. In detail, timing controller 11a outputs timing signal for beam scanning TR to each of first beam source 13 and second beam source 15 in a case where light is incident to first beam source 13 and second beam source 15.

In addition, during the start of a predetermined incidence period, timing controller 11a alternately outputs beam output signal RF to first beam source 13 or second beam source 15. In detail, during the start of the incidence period of an odd number of times, timing controller 11a outputs beam output signal RF to first beam source 13; on the other hand, during the start of the incidence period of an even number of times, outputs beam output signal RF to second beam source 15.

Next, each part of invisible light sensor NVSS is described.

When first beam source 13 as an example of the first light source receives timing signal for beam scanning TR from timing controller 11a of controller 11, reference beam LS1 (for example, near infrared beam) that is a laser beam of invisible light that has a predetermined wavelength (for example, 905 nm) is incident on plant PT via beam scanner 17 according to beam output signal RF from timing controller 11a in each incidence period (default value) of an odd number of times.

Note that, presence or absence of detection of water in plant PT is determined by comparing to the predetermined detection threshold level M. Detection threshold level M may be a predetermined value, may be an arbitrarily set value, and furthermore, may be a value based on intensity of the diffuse reflection light that is acquired in a state in which there is no water (for example, a value in which a predetermined margin is added to a value of intensity of the diffuse reflection light that is acquired in a state in which there is no water). That is, presence or absence of detection of water may be determined by comparing detection result image data that is acquired in a state in which there is no water and detection result image data that is acquired thereafter. In this manner, it is possible to set a threshold level appropriate for an environment in which plant detection camera 1 is installed as detecting threshold level M of presence or absence of water by acquiring intensity of the diffuse reflection light in the state in which there is no water.

When second beam source 15 as an example of the second light source receives timing signal for beam scanning TR from timing controller 11a of controller 11, measuring beam LS2 (for example, infrared beam) that is the laser beam of invisible light that has a predetermined wavelength (for example, 1550 nm) is incident on plant PT via beam scanner 17 according to beam output signal RF from timing controller 11a in each incidence period (default value) of an even number of times. In the present embodiment, measuring beam LS2 that is incident from second beam source 15 is used in determination of presence or absence of detection of water in plant PT. Wavelength 1550 nm of measuring beam LS2 is a wavelength which has a characteristic in which light tends to be absorbed in water (refer to FIG. 6).

Furthermore, plant detection camera 1 detects presence or absence of water at the irradiation position of plant PT that is radiated by reference beam LS1 and measuring beam LS2 based on diffuse reflection light RV1 of reference beam LS1 as reference data for detecting water at the irradiation position of plant PT, and using diffuse reflection light RV2 at the irradiation position of plant PT that is radiated by measuring beam LS2 and diffuse reflection light RV1 of reference beam LS1. Accordingly, plant detection camera 1 is able to detect water of plant PT with high precision using reference beam LS1 and measuring beam LS2 of two types of wavelengths that detect water in plant PT differently and diffuse reflection lights RV1 and RV2 thereof.

Beam scanner 17 two-dimensionally scans reference beam LS1 which is incident from first beam source 13 and measuring beam LS2 which is incident from second beam source 15 with respect to plant PT that is present in a detection area in invisible light sensor NVSS. Thereby, plant detection camera 1 detects presence or absence of water at the irradiation position of plant PT that is radiated by reference beam LS1 and measuring beam LS2 based on diffuse reflection light RV2 that is reflected at the irradiation position of plant PT by measuring beam LS2 and diffuse reflection light RV1 described above.

Figure 3:
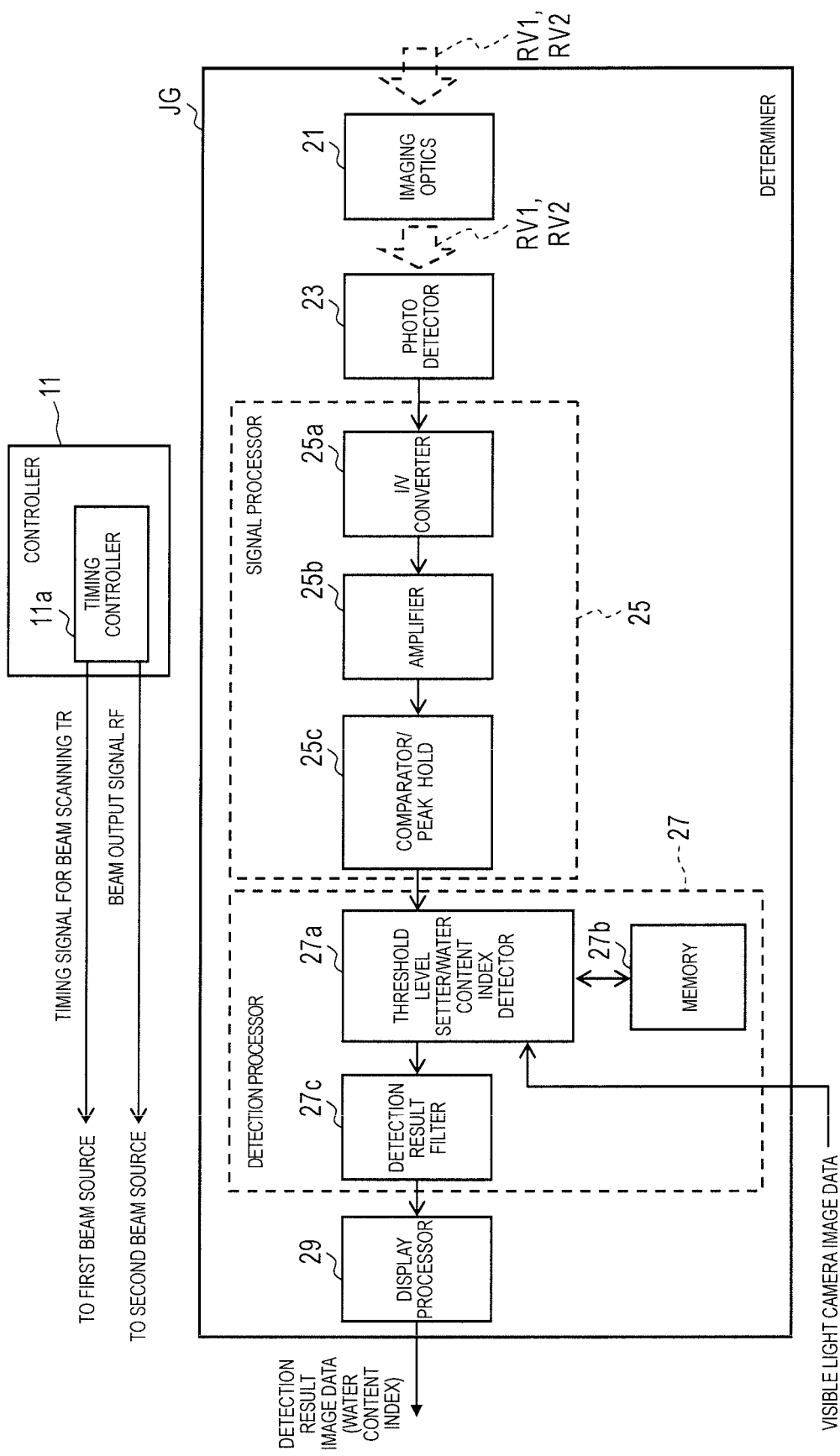
FIG. 3 is a diagram illustrating in detail an example of an internal configuration of a determiner of the plant detection camera.

Next, an internal configuration of determiner JG is described in detail with reference to FIGS. 2 and 3. FIG. 3 is a diagram illustrating in detail an example of an internal configuration of a determiner JG of plant detection camera 1.

Imaging optics 21 is configured using, for example, a single or multiple lenses, light (for example, diffuse reflection light RV1 or diffuse reflection light RV2) which is incident from outside of plant detection camera 1 is concentrated, and diffuse reflection light RV1 or diffuse reflection light RV2 form an image on a predetermined imaging surface of photo detector 23.

Photo detector 23 is an image sensor which has a peak of spectral sensitivity with respect to wavelengths of both of reference beam LS1 and measuring beam LS2. Photo detector 23 converts an optical image of diffuse reflection light RV1 or diffuse reflection light RV2 that form an image on the imaging surface to an electrical signal. Output of photo detector 23 is input to signal processor 25 as the electrical signal (current signal). Note that, imaging optics 21 and photo detector 23 functions as an imaging unit in invisible light sensor NVSS.

Signal processor 25 has I/V converter 25a, amplifier 25b, and comparator/peak hold 25c. I/V converter 25a converts the current signal that is an output signal (analog signal) of photo detector 23 to a voltage signal. Amplifier 25b amplifies a level of the voltage signal that is the output signal (analog signal) of I/V converter 25a up to a processable level in comparator/peak hold 25c.

Comparator/peak hold 25c binarizes the output signal of amplifier 25b and outputs to threshold level setter/water content index detector 27a according to a comparative result of the output signal (analog signal) of amplifier 25b and the predetermined threshold level. In addition, comparator/peak hold 25c includes an analog digital converter (ADC), detects and holds the peak of an analog digital (AD) converter result of the output signal (analog signal) of amplifier 25b and furthermore, outputs peak information to threshold level setter/water content index detector 27a.

Detection processor 27 has threshold level setter/water content index detector 27a, memory 27b, and detection result filter 27c. Threshold level setter/water content index detector 27a as an example of threshold holding unit generates and registers frequency distribution data in advance. Frequency distribution data indicates frequency distribution of the reflection intensity ratio (water content index) in all pixels or one frame image. As will be described later, threshold level setter/water content index detector 27a as a threshold level calculation unit is set by calculating threshold level Sh of the reflection intensity ratio for identifying the shape of the leaf using the frequency distribution data.

In addition, threshold level setter/water content index detector 27a as an example of a water detector detects presence or absence of water at the irradiation position of reference beam LS1 and measuring beam LS2 of plant PT based on output (that is, peak information) of comparator/peak hold 25c in diffuse reflection light RV1 of reference beam LS1 and output (that is, peak information) of comparator/peak hold 25c in diffuse reflection light RV2 of measuring beam LS2.

In detail, threshold level setter/water content index detector 27a temporarily stores, for example, output (that is, peak information) of comparator/peak hold 25c in diffuse reflection light RV1 of reference beam LS1 in memory 27b, and next, waits until the output (that is, peak information) of comparator/peak hold 25c in diffuse reflection light RV2 of measuring beam LS2 is obtained. Threshold level setter/water content index detector 27a obtains output (that is, peak information) of comparator/peak hold 25c in diffuse reflection light RV2 of measuring beam LS2, and then calculates a ratio of output (that is, peak information) of comparator/peak hold 25c in diffuse reflection light RV1 of reference beam LS1 and output (that is, peak information) of comparator/peak hold 25c in diffuse reflection light RV2 of measuring beam LS2 in the same line of plant PT that are contained in the angle of view with reference to memory 27b.

For example, at the irradiation position at which there is water, since a portion of measuring beam LS2 tends to be absorbed, intensity (that is, amplitude) of diffuse reflection light RV2 is attenuated. Accordingly, it is possible for threshold level setter/water content index detector 27a to detect presence or absence of water at the irradiation position of reference beam LS1 and measuring beam LS2 based on a calculation result (for example, calculation result of difference (difference ΔV of amplitude) of each intensity of diffuse reflection light RV1 and diffuse reflection light RV2 or intensity ratio of diffuse reflection light RV1 and diffuse reflection light RV2) of each line of plant PT which is contained in the angle of view.

Note that, threshold level setter/water content index detector 27a may detect presence or absence of water at the irradiation position of reference beam LS1 and measuring beam LS2 of plant PT (refer to FIG. 5) according to a comparison of the size of rate RT of amplitude difference between amplitude VA of diffuse reflection light RV1 of reference beam LS1 and amplitude VB of diffuse reflection light RV2 of measuring beam LS2 (VA-VB) and amplitude VA with predetermined detection threshold level M.

Figure 8:
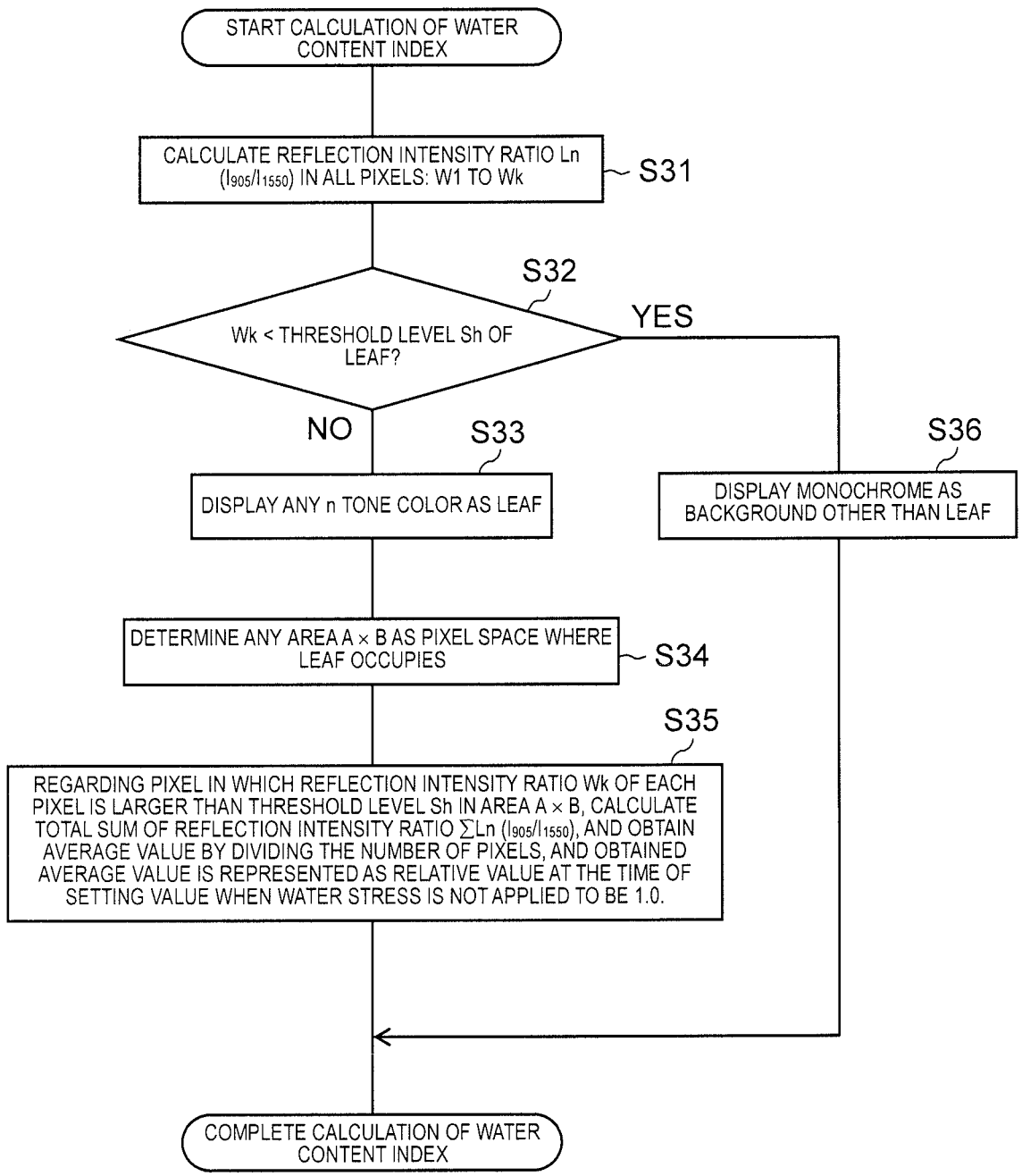
FIG. 8 is a flow chart illustrating a calculation procedure of a water content index in step S18-5.
Figure 29:
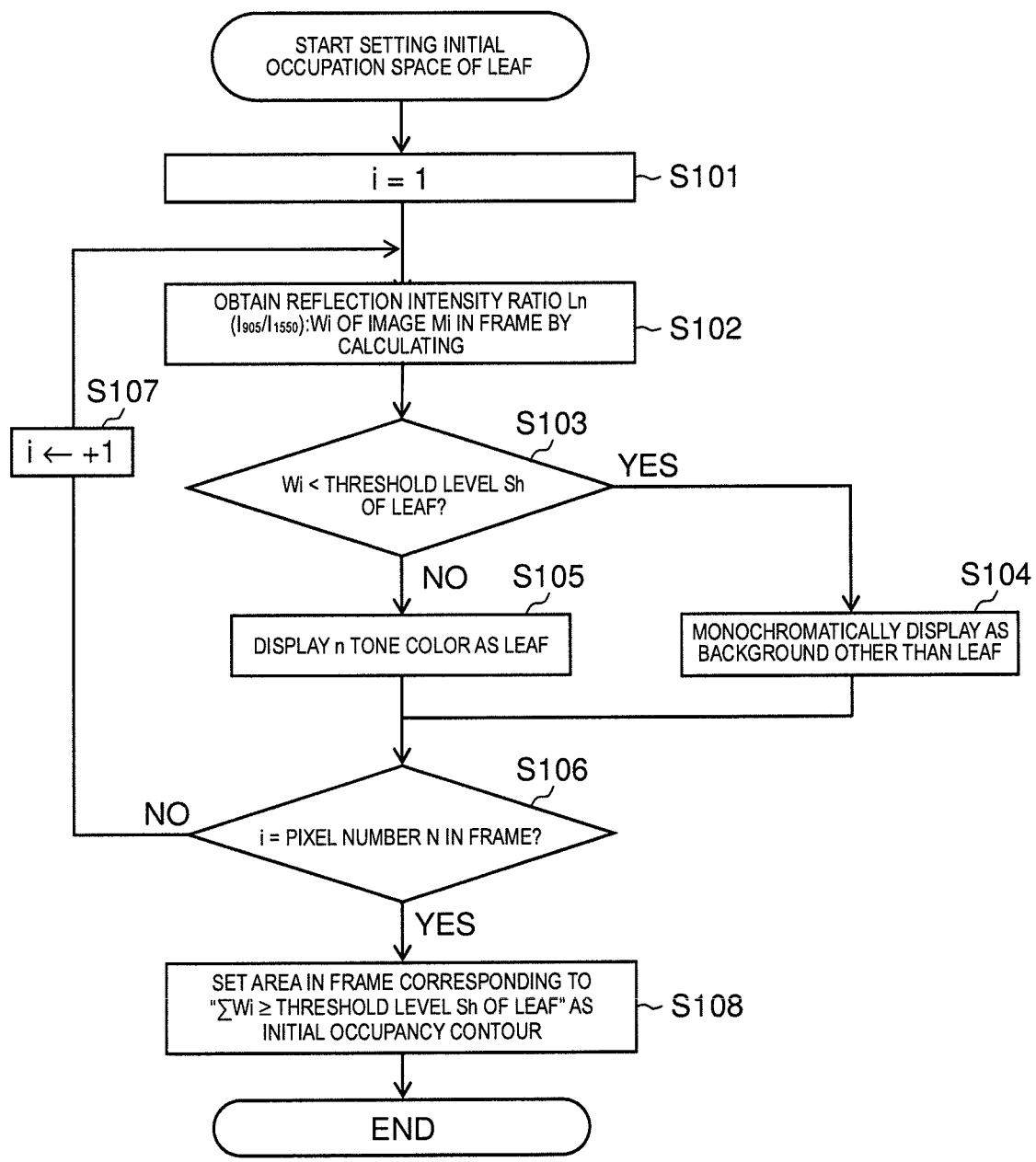
FIG. 29 is a flow chart illustrating an example of an operation procedure for determining the initial occupation contour (outline) of the leaf as a measurement target.

Further, threshold level setter/water content index detector 27a calculates the intensity ratio of diffuse reflection light RV1 to diffuse reflection light RV2, that is, the reflection intensity ratio (also referred to as measurement value) Ln $(I_{905}/I_{1550})$, and obtains the water content index corresponding to the water content contained in the leaf from the total sum of reflection intensity ratio Ln $(I_{905}/I_{1550})$ and an average value obtained by dividing the total sum by the number of pixels constituting a set of pixel areas regarded as the leaf (refer to the description below, for example, FIG. 8 or FIG. 29).

As described above, the pixel area is an area that indicates each pixel constituting the visible light captured image obtained when leaf PT 3 as the observation target of plant detection camera 1 is imaged with visible light or the invisible light image obtained by display processor 29 as a result of irradiation with invisible light (for example, the reference beam LS 1 and the measurement beam LS 2). Details of the water content index will be described below.

Reflection intensity ratio Ln $(I_{905}/I_{1550})$ may be calculated by a predetermined pixel number (4×4 pixels) in all pixels in one frame imaged by visible light camera VSC, and then expressed as reflection intensity ratio W1 to Wk in each predetermined pixel number, or may be calculated for each pixel (=1×1) without performing the calculation for 4×4 pixels.

Memory 27b is configured using, for example, a random access memory (RAM), and temporarily stores output (that is, peak information) of comparator/peak hold 25c in diffuse reflection light RV1 of reference beam LS1.

Detection result filter 27c filters and then extracts information which relates to detection result of water from plant detection camera 1 based on output of threshold level setter/water content index detector 27a. Detection result filter 27c outputs information which relates to the extraction result to display processor 29. For example, detection result filter 27c outputs information which relates to the detection result of water at the irradiation position of reference beam LS1 and measuring beam LS2 of plant PT to display processor 29.

Display processor 29 uses output of detection result filter 27c and generates data of an invisible light image data (detection result image data) that indicates the position of water at the irradiation position at each distance from plant detection camera 1 as an example of information which relates to water at the irradiation position. Display processor 29 as an output unit outputs detection result image data which includes information on distance from plant detection camera 1 to the irradiation position to display controller 37 of visible light camera VSC. The invisible light image data does not need to include information on the distance from plant detection camera 1 to the irradiation position.

Next, each part of visible light camera VSC will be described. Imaging optics 31 is configured using, for example, a lens, ambient light RV0 from in the angle of view of plant detection camera 1 is concentrated, and ambient light RV0 forms an image on a predetermined imaging surface of photo detector 33.

Photo detector 33 is an image sensor which has a peak of spectral sensitivity with respect to wavelength of visible light (for example, 0.4 to 0.7 μm). Photo detector 33 converts an optical image that forms an image on the imaging surface to the electrical signal. Output of photo detector 33 is input to image signal processor 35 as the electrical signal. Note that, imaging optics 31 and photo detector 33 function as an imaging unit in visible light camera VSC.

Image signal processor 35 uses the electrical signal which is output of photo detector 33, and visible light image data is generated which is specified by a user in recognizable red, green, and blue (RGB), brightness and color difference (YUV), and the like. Thereby, visible light image data that is imaged by visible light camera VSC forms visible light camera image data. Image signal processor 35 outputs the visible light image data to display controller 37.

In a case where display controller 37 uses visible light image data that is output from image signal processor 35 and detection result image data that is output from display processor 29, and detects water at any position of the visible light image data, display data in which visible light image data and detection result image data are composited, or display data which comparatively represents the visible light image data and detection result image data are generated as examples of information related to water. Display controller 37 (output unit) prompts display by transmitting display data to data logger DL or communication terminal MT that are connected via, for example, a network.

Data logger DL transmits display data that is output from display controller 37 to communication terminal MT or one or more externally connected device (not shown), and prompts display of display data on a display screen of communication terminal MT or one or more externally connected device (for example, monitor 50 within the control room in the office indicated in FIG. 1).

Communication terminal MT is, for example, a portable communication terminal which is used by an individual user, receives display data that is transmitted from display controller 37 via the network, and displays display data on the display screen of communication terminal MT.

Figure 4:
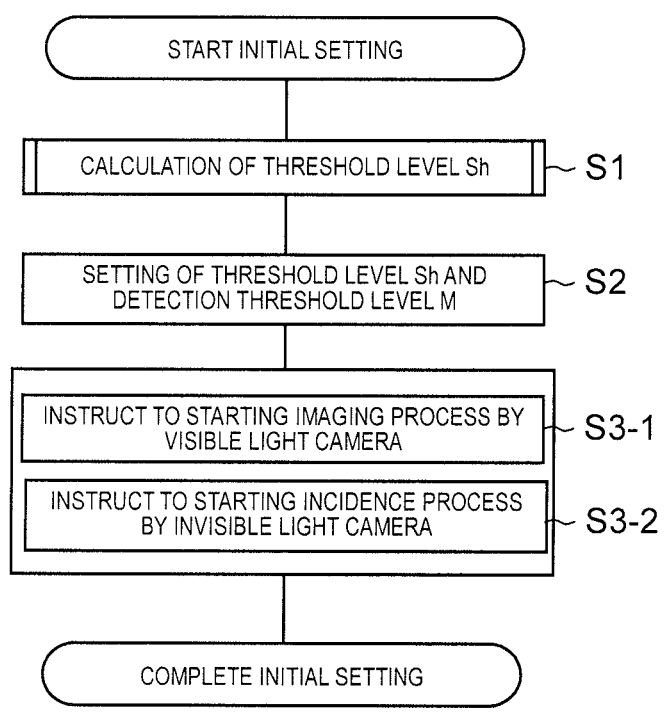
FIG. 4 is a flow chart illustrating an example of an initial setting operation in controller of the plant detection camera.

Description of Example of Initial Operation in Invisible Light Sensor Controller Next, an example of an initial operation in controller 11 of invisible light sensor NVSS of plant detection camera 1 of the present embodiment will be described with reference to FIG. 4. FIG. 4 is a flow chart illustrating an example of an initial setting operation in controller 11 of plant detection camera 1.

When controller 11 instructs settings of threshold level Sh of reflection intensity ratio for identifying the shape of the leaf with respect to threshold level setter/water content index detector 27a, threshold level setter/water content index detector 27a calculates and sets threshold level Sh (S1). Details of the process in which threshold level Sh is set will be described below. Note that, in a case where threshold level Sh is a fixed value, the process of step S1 may be omitted.

In addition, controller 11 sets detection threshold level M of water in detection processor 27 of invisible light sensor NVSS in threshold level setter/water content index detector 27a (S2). It is preferable to appropriately provide detection threshold level M according to a specific substance that is a detection target.

After the process of step S2, controller 11 outputs a control signal for starting an imaging process to each part of visible light camera VSC (S3-1) and outputs to first beam source 13 and second beam source 15 of invisible light sensor NVSS timing signal for beam scanning TR for starting incidence of reference beam LS1 and measuring beam LS2 to first beam source 13 and second beam source 15 (S3-2). Note that, either an execution timing of an operation of step S3-1 or an execution timing of an operation of step S3-2 may be first, or may be simultaneous.

Figure 5:
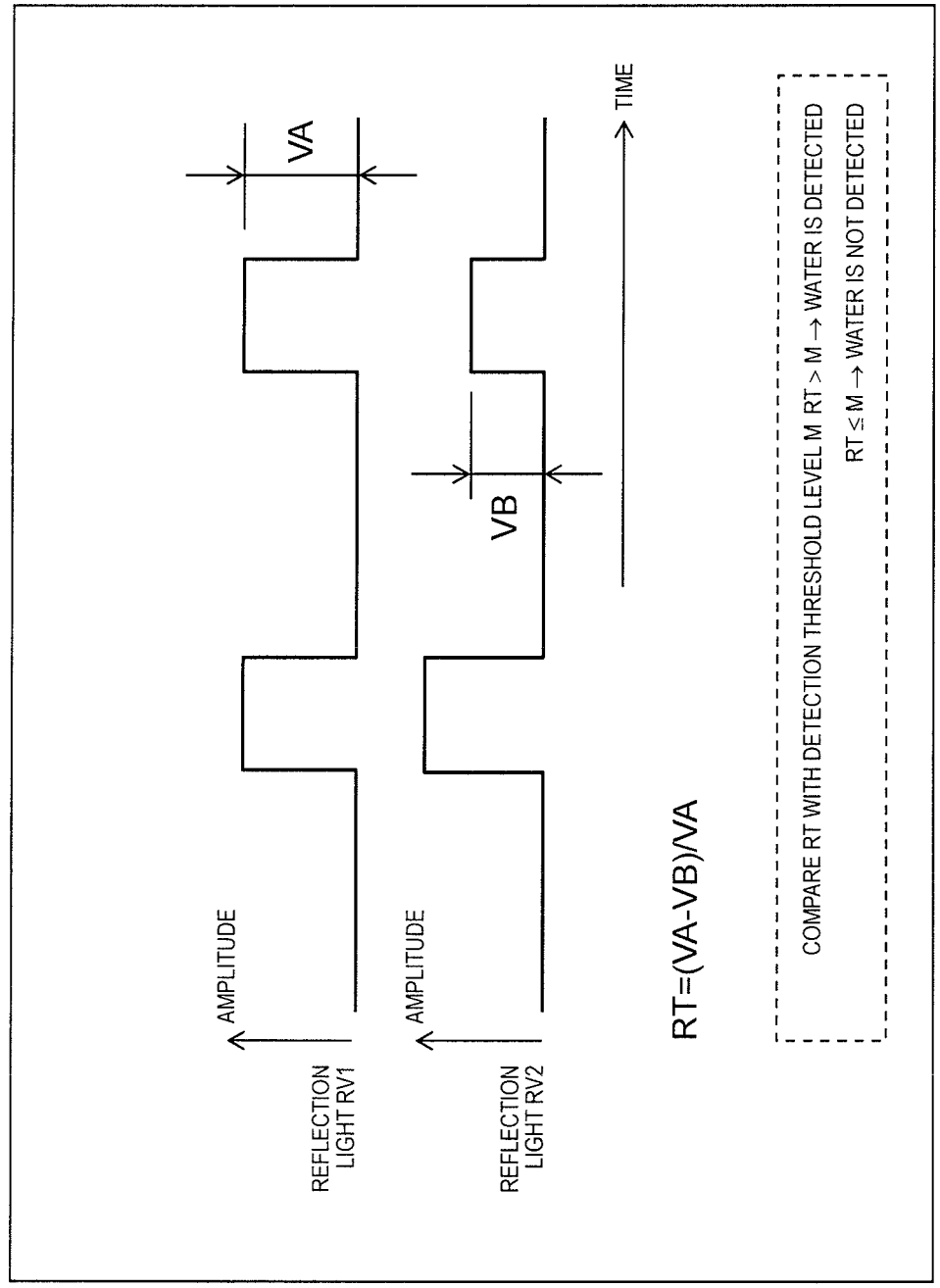
FIG. 5 is a principle explanatory diagram of detection of water in invisible light sensor.

FIG. 5 is a principle explanatory diagram of detection of water in invisible light sensor NVSS. For example, threshold level setter/water content index detector 27a may determine that water is detected if RT>M, and may determine that water is not detected if RT≤M. In this manner, threshold level setter/water content index detector 27a is able to eliminate influence of noise (for example, disturbance light) and is able to detect presence or absence of water with high precision by detecting presence or absence of water according to a comparative result of rate RT between amplitude difference (VA-VB) and amplitude VA and detection threshold level M.

Figure 6:
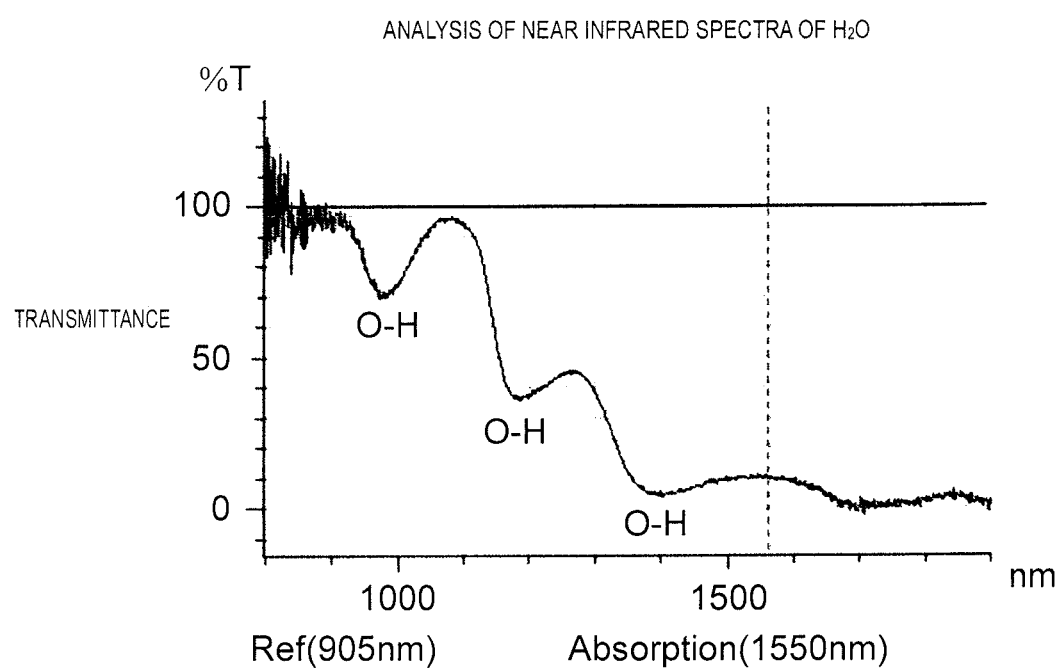
FIG. 6 is a graph illustrating an example of the near infrared spectra of water ($H_2O$).

FIG. 6 is a graph illustrating an example of the near infrared spectra of water ($H_2O$). A horizontal axis of FIG. 6 indicates wavelength (nm), and a vertical axis of FIG. 6 indicates transmittance (transparency) (%). As shown in FIG. 6, since reference beam LS1 of wavelength 905 nm has transmittance in water ($H_2O$) that is close to 100%, it is understood that reference beam LS1 has a characteristic in which light tends not to be absorbed in water. In the same manner, since measuring beam LS2 of wavelength 1550 nm has transmittance in water ($H_2O$) that is close to 10%, it is understood that measuring beam LS2 has a characteristic of tending to be absorbed in water. Therefore, in the present embodiment, the wavelength of reference beam LS1 which is incident from first beam source 13 is 905 nm, and the wavelength of measuring beam LS2 which is incident from second beam source 15 is 1550 nm.

Even in a case where the projection range of the near infrared beam is decreased as the leaf withers, or the leaf is warped or rolled up to increase the thickness of the leaf, in the present embodiment, an average value (hereinafter, referred to as "pixel average water content index") obtained by dividing a total sum of the reflection intensity ratio in all the pixel areas (that is, each pixel) constituting the invisible light image of the leaf by the number of pixels, and a total sum (hereinafter, referred to as "total sum of the water content index") for each pixel of the reflection intensity ratio in all the pixels constituting the invisible light image of the leaf by the number of pixels are used as indexes of the water content. Further, a value of the pixel average water content index when the water stress is not applied (that is, at an initial stage) and a value of the total sum of the water content index which are standardized and indicated as 1.0 are referred to as the standardized pixel average water content index (or simply referred to as "water content index") and the total sum of the standardized water content index. In this way, by expressing the initial value 1.0 with relative value, it is possible to easily perform relative comparison of temporal changes of "pixel average water content index" and "total sum of the water content index" of leaves having different angle and leaf thickness. These pixel average water content index and the total sum of the water content index are calculated by using the reflection intensity ratio calculated for each pixel constituting the invisible light image of the leaf. Accordingly, the pixel average water content index is represented by "$(1/\text{number of pixels constituting invisible light image of leaf}) \times \Sigma \text{ Ln } (I_{905}/I_{1550})$", the total sum of the water content index is represented by "$\Sigma \text{ Ln } (I_{905}/I_{1550})$", and both have a strong correlation with the water potential (in other words, the amount of water stress applied to plants). Note that, all the pixel areas constituting the invisible light image of the leaf are, for example, a set of areas where the pixel value (that is, the value of the reflection intensity ratio in the pixels corresponding to the positions where reference beam LS1 and measuring beam LS2 are radiated) is greater than threshold level Sh at the beginning of the measurement period. Note that, threshold level Sh may be a predetermined value, or may be calculated by using a method illustrated in FIG. 31 described below.

In addition, the above-described pixel average water content index or the total sum of the water content index are defined by using the reflection intensity ratio in all the pixel areas (that is, each pixel) constituting the invisible light image of the leaf, and also may be defined by matching the visible light captured image and the invisible light image of the leaves each other in size by using the reflection intensity ratio at the pixel corresponding to green (G) of the visible light image. More specifically, the pixel average water content index may be an average value obtained by dividing the total sum of the reflection intensity ratios of all the pixels corresponding to green (G) of the visible light captured image of leaves by the number of pixels. Similarly, the total sum of the water content index may be set as the total sum of the reflection intensity ratios of all the pixels corresponding to green (G) of the visible light captured image of leaves.

Figure 7:
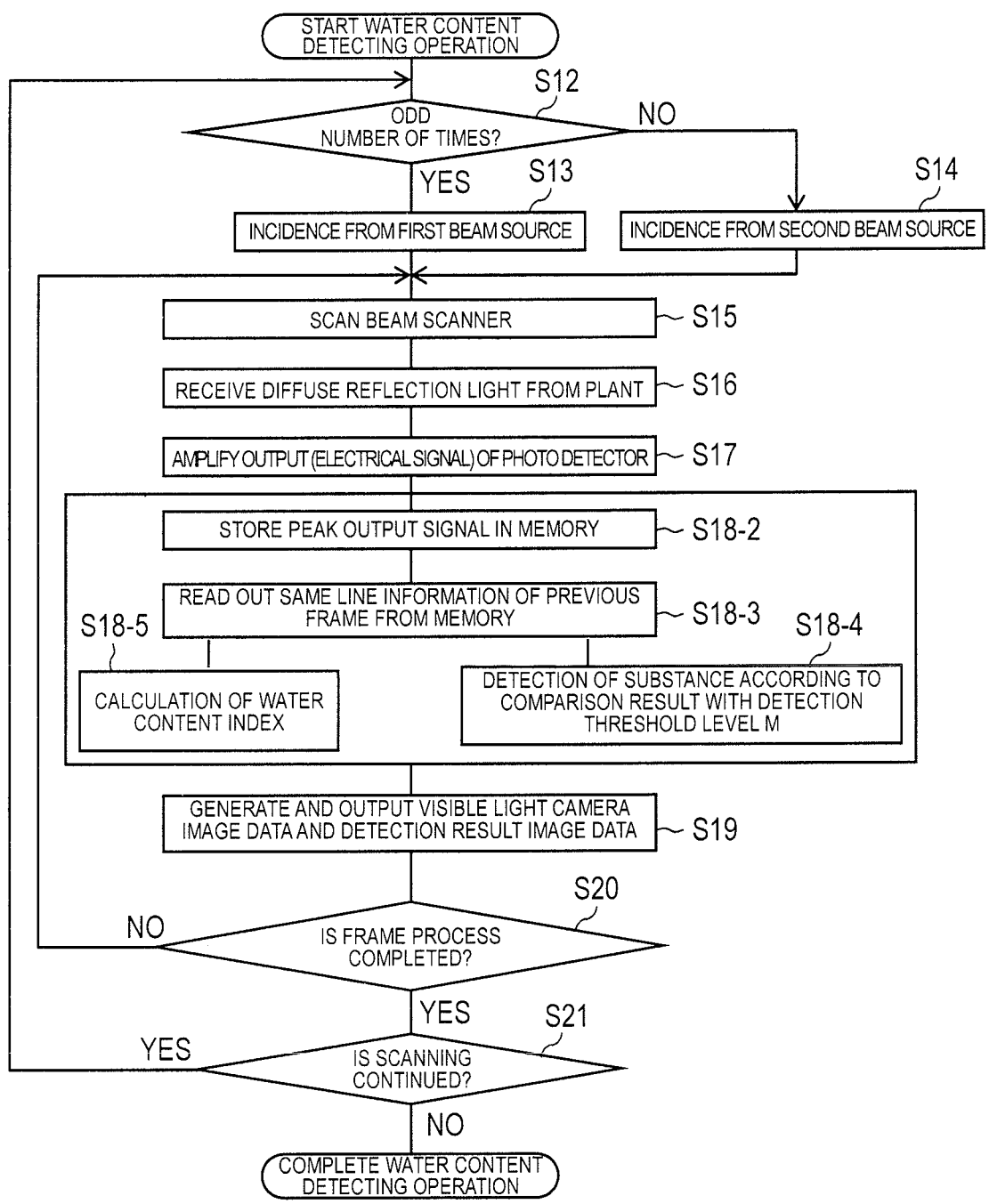
FIG. 7 is a flow chart illustrating a detailed operation procedure which relates to detection of water that is contained in a leaf of a plant in an invisible light sensor.

Description of Detailed Operation Relating to Detection of Water and Undulation of Invisible Light Sensor Next, a detailed operation procedure which relates to detection of water in invisible light sensor NVSS of plant detection camera 1 will be described with reference to FIG. 7. FIG. 7 is a flow chart illustrating a detailed operation procedure which relates to detection of water that is contained in leaf PT3 of plant PT in invisible light sensor NVSS. As a premise of description of the flow chart illustrated in FIG. 7, timing controller 11a outputs timing signal for beam scanning TR to first beam source 13 and second beam source 15, and reference beam LS1 or measuring beam LS2 from plant detection camera 1 is radiated toward leaf PT3 of plant PT.

In FIG. 7, controller 11 determines whether or not beam output signal RF in incidence period of an odd number of times is output from timing controller 11a (S12). In a case where controller 11 determines that beam output signal RF in incidence period of an odd number of times is output from timing controller 11a (YES in S12), first beam source 13 incidents reference beam LS1 according to beam output signal RF from timing controller 11a (S13). Beam scanner 17 one-dimensionally scans reference beam LS1 of one line or more in an X direction of plant PT which is contained in the angle of view of plant detection camera 1 (S15). At the irradiation position on each line in the X direction on which the reference beam LS1 is radiated, diffuse reflection light RV1 that is generated by reference beam LS1 being diffused and reflected is received by photo detector 23 via imaging optics 21 (S16).

In signal processor 25, output (electrical signal) in photo detector 23 of diffuse reflection light RV1 is converted to the voltage signal, and the level of the voltage signal is amplified up to a processable level in comparator/peak hold 25c (S17). Comparator/peak hold 25c binarizes the output signal of amplifier 25b and outputs to threshold level setter/water content index detector 27a according to a comparative result of the output signal of amplifier 25b and the predetermined threshold level. Comparator/peak hold 25c outputs peak information of output signal of amplifier 25b to threshold level setter/water content index detector 27a.

Threshold level setter/water content index detector 27a temporarily stores output (that is, peak information) of comparator/peak hold 25c with respect to diffuse reflection light RV1 of reference beam LS1 in memory 27b (S18-2). In addition, threshold level setter/water content index detector 27a reads from memory 27b output of comparator/peak hold 25c with respect to the same line in diffuse reflection light RV1 or diffuse reflection light RV2 with respect to reference beam LS1 or measuring beam LS2 in a previous frame (incidence period) that is stored in memory 27b (S18-3).

Threshold level setter/water content index detector 27a detects presence or absence of water on the same line based on output (that is, peak information) of comparator/peak hold 25c in diffuse reflection light RV1 of reference beam LS1 and output (that is, peak information) of comparator/peak hold 25c in diffuse reflection light RV2 of measuring beam LS2 on the same line and predetermined detection threshold level M (S18-4).

Threshold level setter/water content index detector 27a calculates a water content index which is a total sum $\Sigma \text{ Ln } (I_{905}/I_{1550})$ of the reflection intensity ratio (S18-5). Details of calculation of the water content index will be described below.

Display processor 29 uses output of detection result filter 27c and generates detection result image data that indicates the detection position of water. Display controller 37 outputs detection result image data that is generated by display processor 29 and visible light camera image data of a visible light image that is imaged by visible light camera VSC (S19). Each operation of steps S15, S16, S17, S18-2 to S18-5, and S19 is executed in each line within the detection area of one frame (incidence period).

That is, when each operation of steps S15, S16, S17, S18-2 to S18-5, and S19 is complete with respect to one line in the X direction, each operation of steps S15, S16, S17, S18-2 to S18-5, and S19 is performed with respect to a subsequent line in the X direction (NO in S20), hereinafter until each operation of steps S15, S16, S17, S18-2 to S18-5, and S19 is complete in one frame, each operation of steps S15, S16, S17, S18-2 to S18-5, and S19 is repeated.

Meanwhile, in a case where execution of each operation of steps S15, S16, S17, S18-2 to S18-5, and S19 is complete with respect to all lines in one frame (YES in S20), and in a case where scanning of incident light is continued (YES in S21), an operation of invisible light sensor NVSS returns to step S12. Meanwhile, in a case where scanning of reference beam LS1 and measuring beam LS2 is not continued (NO in S21), the operation of invisible light sensor NVSS is complete.

FIG. 8 is a flow chart illustrating a calculation procedure of a water content index in step S18-5. Threshold level setter/water content index detector 27a calculates the reflection intensity ratio of $\Sigma$ Ln $(I_{905}/I_{1550})$ in all pixels from the frame image (S31). Here, a measurement value of reflection intensity ratio Ln $(I_{905}/I_{1550})$ of each pixel is represented by reflection intensity ratios W1 to Wk. For example, in a case where the image of the near infrared beam is configured from 76,800(=320×240) pixels, a suffix k of Wk is a variable which represents 1 to 76,800.

Threshold level setter/water content index detector 27a determines whether or not a pixel value (that is, reflection intensity ratio Wk) for each pixel is larger than threshold level Sh for identifying leaf PT3 (S32). An initial value of threshold level Sh is registered in advance in threshold level setter/water content index detector 27a as an empirical value. The empirical value is determined according to a specification of the device for observing water content (intensity of the irradiation laser beam, sensitivity of a light receiving element, and the like), water content (approximately 90%) of the leaf that is the measurement target, thickness of the leaf (for example, 200 μm), inside/outside (or "indoor/outdoor"), and the like. In particular, in a case of outside, there is change according to how sunlight hits or manner of growth of foliage, and the variable is changed each time.

For example, as the empirical value, in the case of an imaging distance of 1 m, threshold level Sh during imaging inside is set to approximately 0.3. Threshold level Sh during imaging outside is set to approximately 0.9. In addition, in the case of an imaging distance of 3 m, threshold level Sh during imaging inside is set to approximately 0.05. It is preferable to change threshold level Sh in a case where threshold level Sh is set as the initial value, it is determined whether or not the threshold level is optimal in comparison to the actual shape of the leaf, and the threshold level is not optimal. In addition, as will be described later, a calculation process of threshold level Sh is performed, and it is possible to register calculated threshold level Sh as the initial value.

In step S32, in a case where reflection intensity ratio Wk is less than threshold level Sh, the pixel is a pixel (in other words, pixels that are not pixels constituting the visible light image area regarded as a leaf) that represents a background other than the leaf, and display processor 29 generates monochromatic display data for displaying pixels monochromatically (S36).

Meanwhile, in step S32, in a case where reflection intensity ratio Wk is threshold level Sh or more (threshold level or more), display processor 29 displays pixels in a tone color corresponding to reflection intensity ratio Ln $(I_{905}/I_{1550})$ (S33). Here, it is possible to display the tone color corresponding to reflection intensity ratio Ln $(I_{905}/I_{1550})$ at n tone. n is an arbitrary positive number.

FIG. 27 is a diagram illustrating a table that indicates tone color corresponding to reflection intensity ratio. In table Tb, reflection intensity ratio Ln $(I_{905}/I_{1550})$ and the intensity ratio converted value (reflection light at 905 nm/reflection light at 1550 nm) are divided for each to color.

In detail, in a case where reflection intensity ratio Ln $(I_{905}/I_{1550})$ is less than 0.3, that is, in a case of being threshold level Sh of the leaf or less, the pixel is displayed using, for example, white (monochrome). Meanwhile, in a case where reflection intensity ratio Ln $(I_{905}/I_{1550})$ is 0.3 to less than 0.4, the pixel is displayed using, for example, dark green. In the same manner, in a case of being 0.4 to less than 0.5, the pixel is displayed using green. In a case of being 0.5 to less than 0.55, the pixel is displayed using yellow. In a case of being 0.55 to less than 0.6, the pixel is displayed using orange. In a case of being 0.6 to less than 0.75, the pixel is displayed using red. In a case of being 0.75 or more, the pixel is displayed using purple. In this manner, the color of the pixel that belongs to the leaf is set in any of six tones.

Note that, in a case where a pixel space which the leaf occupies is not appropriate in comparison to the actual shape of the leaf, the user may set threshold level Sh up or down in each predetermined increment (for example, 0.01). Alternatively, the user may set appropriate threshold level Sh by activating a process in which threshold level Sh described later is automatically set.

Threshold level setter/water content index detector 27a specifies an area of the pixel space which the leaf occupies (S34). FIG. 28 is a diagram illustrating a table that indicates the reflection intensity ratio in a portion of a frame image including a pixel space occupied by the leaf. In this table, as a portion of the frame image, reflection intensity ratio Ln $(I_{905}/I_{1550})$ for 21×9 pixels is indicated. A pixel whose background is black (dot display) corresponds to a pixel of a leaf.

As described above, the pixels of the leaf are pixels in which reflection intensity ratio Ln $(I_{905}/I_{1550})$ exceeds threshold level Sh (here, 0.3). In addition, area ARE of a rectangle (A×B) is specified such that the pixels of the leaf are enclosed. The area ARE is used as a value which determines the size of the leaf.

Note that, the size of the leaf may represent the pixel number which exceeds threshold level Sh.

Threshold level setter/water content index detector 27a (water content calculation unit) calculates the total sum of the water content index $\Sigma$ Ln $(I_{905}/I_{1550})$ that is a sum total of reflection intensity ratio Ln $(I_{905}/I_{1550})$ where a measurement value (reflection intensity ratio Ln $(I_{905}/I_{1550})$) is larger than threshold level Sh in area ARE (S35). The total sum of the water content which is contained in the entirety of the leaf is understood by obtaining water content index $\Sigma$ Ln $(I_{905}/I_{1550})$.

Furthermore, in step S35, it is possible for threshold level setter/water content index detector 27a to calculate the number of pixels in which the measurement value (reflection intensity ratio Ln $(I_{905}/I_{1550})$) is larger than threshold level Sh in area ARE, and calculate an average value (referred to as pixel average water content index) by dividing total sum $\Sigma$ Ln $(I_{905}/I_{1550})$ of the reflection intensity ratio by the number of calculated pixels. The average value is a value in which the total sum of the reflection intensity ratio is divided by the area of the leaf where the external form (outline) of the leaf is determined by threshold level Sh, and a value in which the total sum of the reflection intensity ratio in a spot is divided by a fixed area of the spot are different. After this, the calculation operation of the water content index ends.

In this manner, in the present embodiment, the reflection intensity ratio of each irradiation position is not obtained, the reflection intensity ratio of each pixel in the frame image is obtained, and it is possible to correctly calculate the water content index from the total sum of reflection intensity ratio of each pixel. Accordingly, it is possible to accurately determine status of the leaf, that is, the plant.

Figure 30A:
FIG. 30A is a frame image that images stems and leaves of a tomato.
Figure 30B:
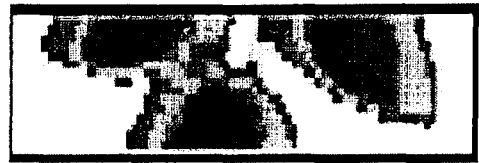
FIG. 30B is a diagram illustrating the occupancy space of the leaf which is obtained in a case where the imaging distance is set to 3 m and a threshold level is set to 0.05 with respect to the visible light image in FIG. 30A.
Figure 30C:
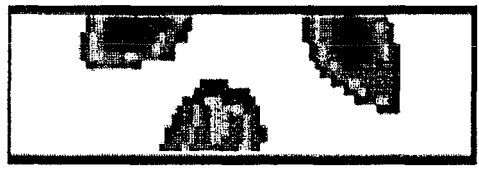
FIG. 30C is a diagram illustrating the occupancy space of the leaf which is obtained in a case where the imaging distance is set to 1 m and a threshold level is set to 0.3 with respect to the visible light image in FIG. 30A.

Here, as described above, threshold level Sh of the leaf is set to a subsequent value as the initial value. In a case where plant detection camera 1 is installed inside and leaf PT3 is imaged inside, and in a case where imaging distance is empirically 1 m, threshold level Sh is set to approximately 0.3. In the case of an imaging distance of 3 m, threshold level Sh is set to approximately 0.05. Meanwhile, in a case of imaging outside, since a condition is fluctuated, threshold level Sh is empirically set to approximately 0.9. FIGS. 30A to 30C are diagrams illustrating an occupancy range of the leaf. FIG. 30A is a frame image that images stems and leaves of a tomato. A distance between leaves is approximately 1 cm. FIG. 30B illustrates the occupancy space of the leaf which is obtained in a case where the imaging distance is set to 3 m and threshold level Sh is set to 0.05 with respect to the visible light image in FIG. 30A. In this case, it is understood that the leaves overlap in portions and threshold level Sh (=0.05) is a value that is inappropriately set. FIG. 30C illustrates the occupancy space of the leaf which is obtained in a case where the imaging distance is set to 1 m and threshold level Sh is set to 0.3 with respect to the visible light image in FIG. 30A. In this case, the outer form of the leaf does not overlap with another leaf, in addition, the occupancy space of the leaf is the same as the size of the outer form of the leaf of the visible light image. In this case, it is understood that threshold level Sh (=0.3) is a value that is correctly set.

Figure 31:
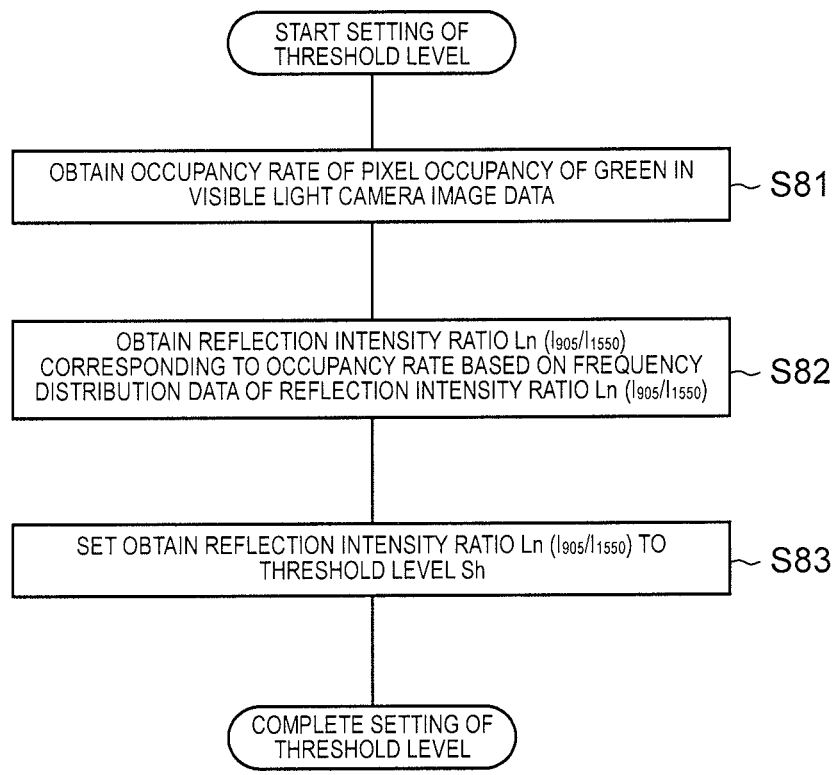
FIG. 31 is a flow chart illustrating a threshold level setting procedure.

In addition, threshold level Sh of the leaf may not be registered before the subsequent process is performed and the calculation process of the water content index indicated in FIG. 8 is executed. FIG. 31 is a flow chart illustrating a threshold level setting procedure.

Threshold level setter/water content index detector 27a obtains an occupancy rate that is determined as the leaf (G pixel number/all pixel numbers), i.e. a pixel occupancy of green (G) that is determined as the color of the leaf with respect to the frame image (for example, refer to FIG. 30A) that is imaged by visible light camera VSC (S81).

Figure 32:
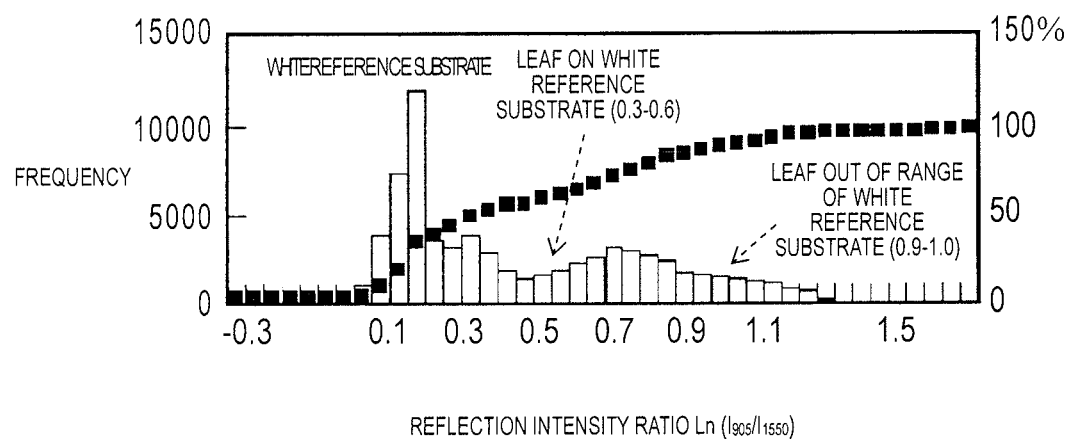
FIG. 32 is a graph illustrating frequency distribution of a reflection intensity ratio in all pixels.

Threshold level setter/water content index detector 27a obtains the water content index corresponding to the occupancy rate of the leaf based on frequency distribution data of the water content index (S82). FIG. 32 is a graph illustrating the frequency distribution of the reflection intensity ratio in all pixels. Frequency distribution data is registered in threshold level setter/water content index detector 27a. When using the frequency distribution data, in a case where, for example, the occupancy rate that is determined as the pixel occupancy of green (G) that is determined as the color of the leaf is 52%, the water content index is approximately 0.3.

Threshold level setter/water content index detector 27a sets the water content index that is obtained in step S82 to threshold level Sh (S83). After this, threshold level setter/water content index detector 27a ends the present process.

In this manner, it is possible to correctly determine the outer form of the leaf by obtaining an occupancy pixel number of green (specified color) of the leaf and threshold level Sh corresponding to cumulative frequency of Ln ($I_{905}/I_{1550}$) that is the measurement value which is the same pixel number by utilizing the visible light image that is imaged by visible light camera VSC, that is, by modifying the threshold level of the water content of each pixel that is contained in the leaf. Accordingly, it is possible to accurately calculate the average value of the pixel unit by correctly determining the outer form of the leaf. In contrast to this, in a case where the fixed area of the spot or the outer form of the visible light image is used, when the outer form of the leaf is not correctly captured, a large error is generated in the average value of the pixel unit.

Figure 9:
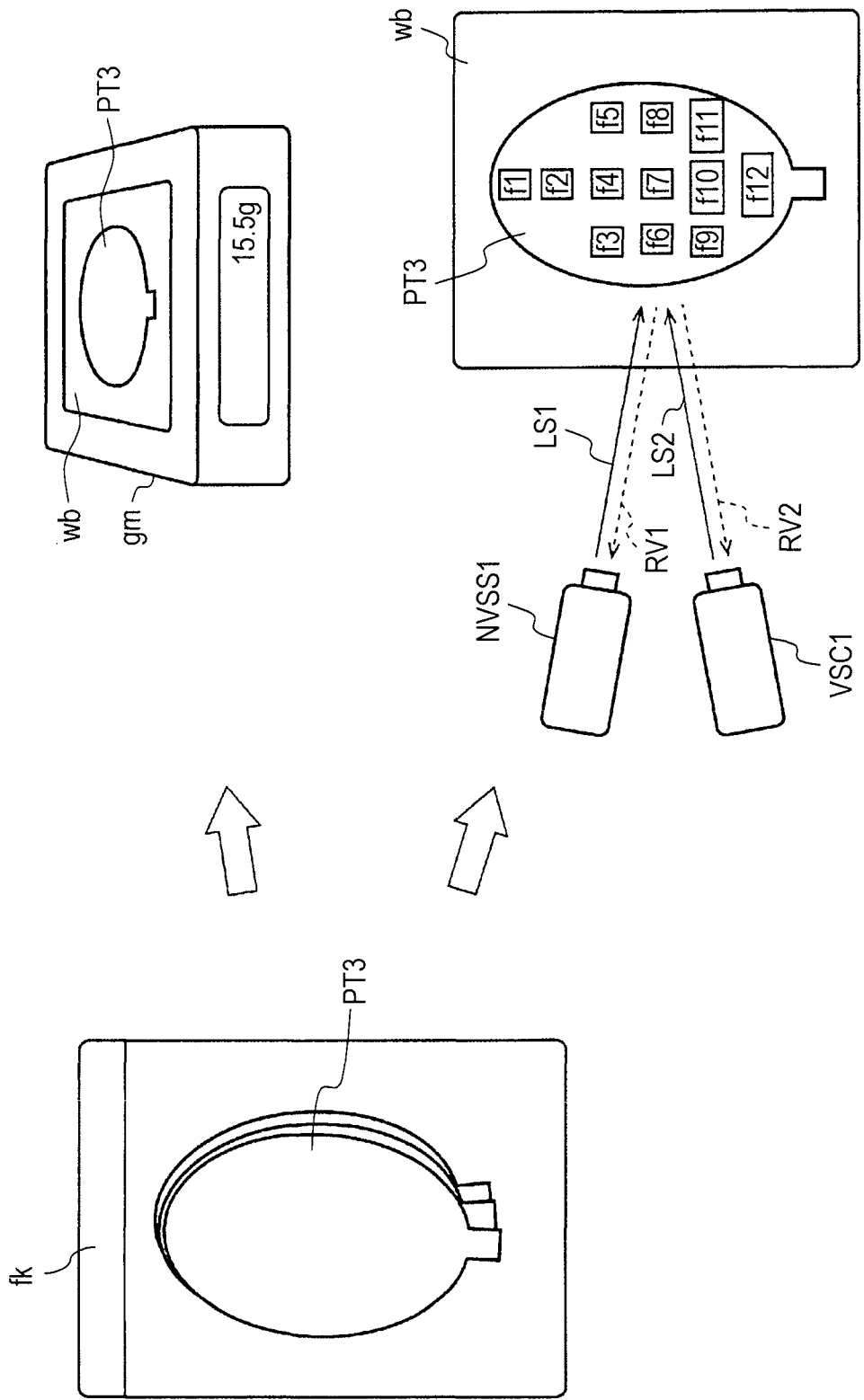
FIG. 9 is a diagram illustrating an example of the method of measuring Comparative Examples.

Here, Comparative Examples will be described for another method of measuring the water content in the leaf. FIG. 9 is a diagram illustrating an example of the method of measuring Comparative Examples. Macrophyll leaf PT3 that is sealed and packed in vinyl bag fk is taken out and fixed to white board wb such that leaf PT3 does not move. White board wb that is firmly fixed to leaf PT3 is placed on weight scale gm, and the weight is measured. At this time, since the weight of white board wb is measured in advance, and is adjusted by 0 points, the weight of the leaf is displayed on a meter of weight scale gm. Change of weight due to transpiration of the leaf is measured while the time elapses. After all measurement ends, the leaf completely dries and the weight is obtained. The average water content of the leaf during measurement is obtained by deducting the weight of the leaf during drying from the weight of the leaf during measurement. The average water content of the leaf substantially lowers while the time elapses.

On the other hand, in the present embodiment, at the time of measuring the water content of the leaf, a background material is disposed so as to cover a back surface (rear side) of the leaf that is the measurement target. As the material of the background material, a material that does not contain water and that does not deform due to pesticide, sprinkling, or $CO_2$ spraying is given such as plastic, coated paper, sheets such as aluminum foil (plate), a plate, or a block. In addition, it is desirable that the size of the background material has a large surface such that the leaf that is the measurement target is covered and is a size so as not to interfere with photosynthesis of another leaf within two times the projection area of the leaf that is the measurement target. In addition, it is preferable that the thickness of the background material is a thickness of 50 μm to 1 mm self-supporting without curling, and in particular, 50 to 200 μm. In addition, in a case of being supported by the stalk of the leaf, it is preferable that the weight of the background material is a weight to a degree that the leaf does not wilt. In addition, it is preferable that the color of the background material is white or silver with high reflectance of visible light and the near infrared beam.

In the present embodiment, as the background material, a case of using a white reference substrate is indicated. Note that, a white plastic plate, an aluminum plate, a standard white plate, white paper, and the like are given as the white reference substrate.

Figure 10A:
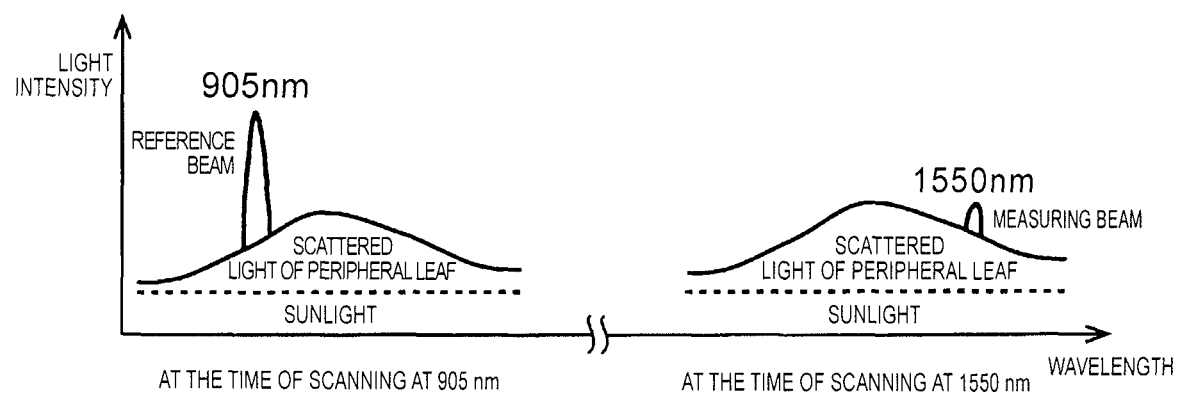
FIG. 10A is a graph illustrating an example of the reflection light intensity with respect to wavelength of the near infrared beam when near infrared beam is radiated toward the leaf outdoors.

FIG. 10A is a graph illustrating an example of the reflection light intensity with respect to wavelength of the near infrared beam when near infrared beam is radiated toward the leaf outdoors. The vertical axis indicates intensity of the near infrared beam which is detected by invisible light sensor NVSS, and the horizontal axis indicates wavelength of a near infrared area. Intensity of light that is scattered by the peripheral leaf other than intensity of light according to sunlight is included in intensity of the near infrared beam which is detected by invisible light sensor NVSS. That is, a rise of the background due to multiple scattering of sunlight being carried out on the peripheral leaf is included in the intensity of the detected near infrared beam. In addition, intensity of light detected by invisible light sensor NVSS is small due to the near infrared beam which has a wavelength of 1550 nm being absorbed by the peripheral leaf. Accordingly, the value of reflection intensity ratio Ln ($I_{905}/I_{1550}$) is large. Therefore, in a case where water content of the leaf outside is measured, it is necessary to set the value of threshold level Sh that is compared to reflection intensity ratio Ln ($I_{905}/I_{1550}$) to be large.

Figure 10B:
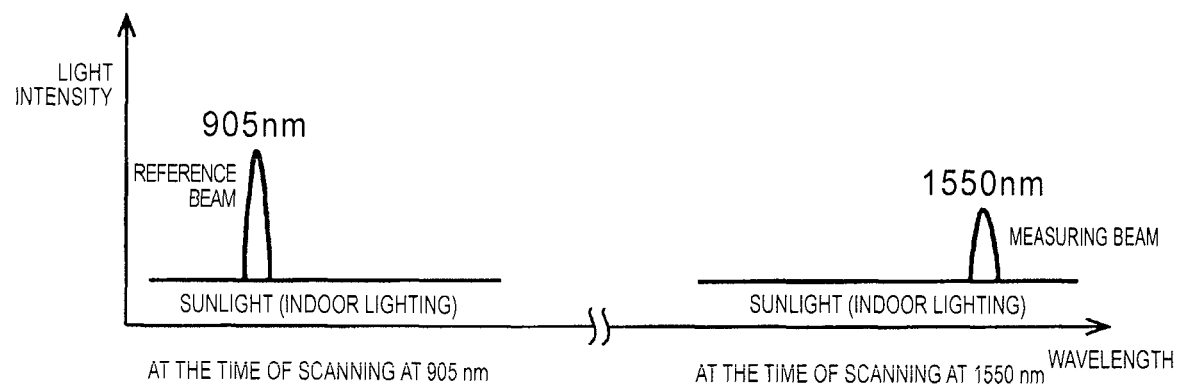
FIG. 10B is a graph illustrating an example of the reflection light intensity with respect to wavelength of the near infrared beam when near infrared beam is radiated toward the leaf on which white reference substrate bd is installed indoors and outdoors.

FIG. 10B is a graph illustrating an example of the reflection light intensity with respect to wavelength of the near infrared beam when near infrared beam is radiated toward the leaf on which white reference substrate bd is installed indoors and outdoors.

The vertical axis indicates intensity of the near infrared beam which is detected by invisible light sensor NVSS, and the horizontal axis indicates wavelength of a near infrared area.

Multiple scattering from the leaf surrounding leaf PT3t that is a measurement target does not occur due to white reference substrate bd being disposed to cover the back surface (rear side) of leaf PT3t that is the measurement target. Accordingly, a lowering of intensity of the near infrared beam which has a wavelength of 1550 nm does not occur. In addition, in the case of inside, a rise of the background does not occur. Note that, in a case of measuring outside, threshold level Sh is set to approximately 0.5. In addition, in a case of measuring inside, threshold level Sh is set to approximately 0.3.

In a case where white reference substrate bd is disposed on the back surface of leaf PT3t that is the measurement target, the leaf may be disposed without being fixed, and leaf PT3t may be attachably fixed to white reference substrate bd. Here, a case where leaf PT3t is attached to white reference substrate bd is illustrated. In each embodiment including the present embodiment, as seen from first beam source 13 and second beam source 15 of plant detection camera 1, white reference substrate bd is disposed on the back of at least one leaf that is the measurement target.

FIG. 11 is a diagram which describes an example of attachment of leaf PT3t on white reference substrate bd. White reference substrate bd is a white plastic plate which has a vertical rectangular shape. Aperture bd1 that is hollowed out in a rectangular shape is formed in the center of white reference substrate bd. In addition, round hole bd2 is formed in an upper portion of white reference substrate bd. Slit bd21 which reaches up to an upper end surface is formed on hole bd2. In addition, three slits bd3, bd4, and bd5 are respectively formed on the lower side and both sides of aperture bd1 that is formed on white reference substrate bd.

In a case where leaf PT3t is attached to white reference substrate bd, a tip end of leaf PT3t is inserted into one of three slits bd3, a void is generated by shifting horizontal white reference substrate bd in a longitudinal direction centered on slit bd21, stalk PT2 of the leaf passes inside, and stalk PT2 is fixed to hole bd2.

Next, control experiment for the water potential contained in the leaf is performed as the observation of the water content contained in the leaf of plant PT by using plant detection camera 1 of the present embodiment, and the sugar content in the leaf due to the water stress obtained by the result of the experiment is considered.

Figure 12:
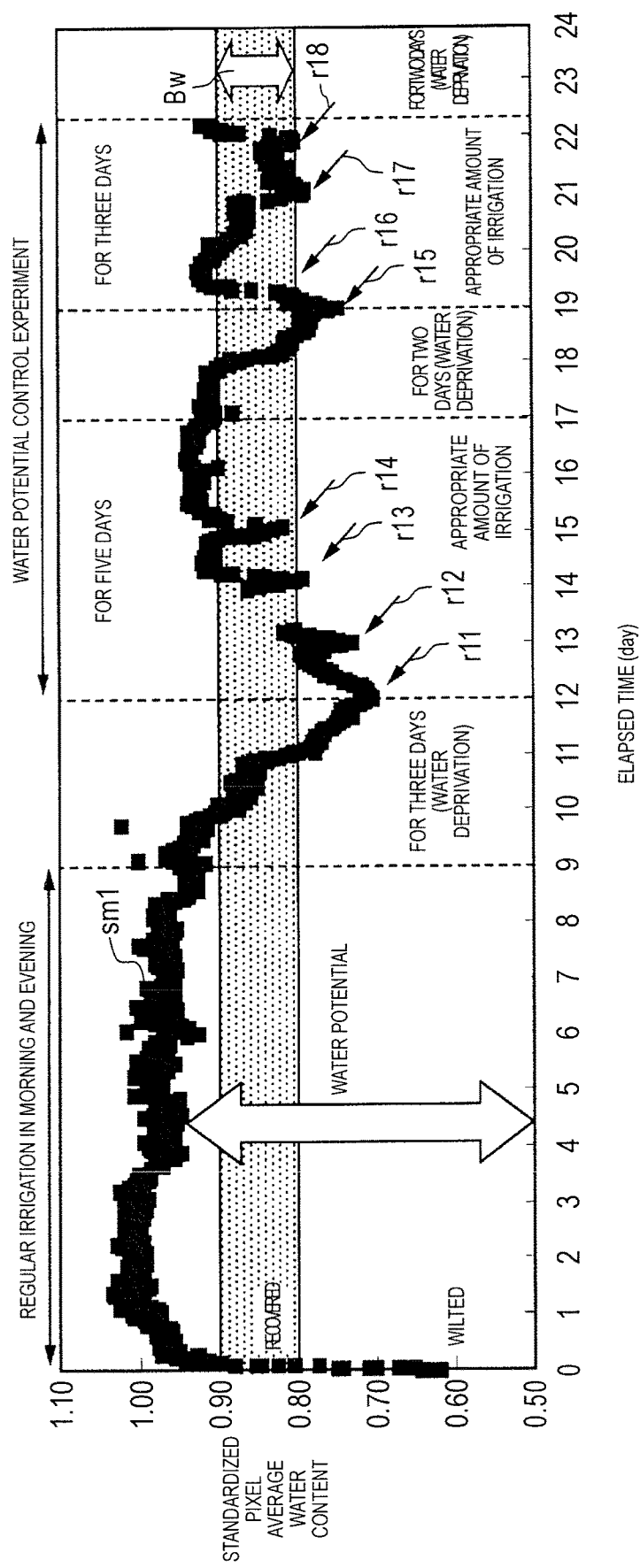
FIG. 12 is a graph illustrating an example of a time-transition of a standardized pixel average water content index in a first water potential control experiment.

FIG. 12 is a graph illustrating an example of a time-transition of standardized pixel average water content index Dw in the first water potential control experiment. The vertical axis of the graph indicates a standardized pixel average water content index. The standardized pixel average water content index represents a water potential as an index of the water content contained in the leaf that is a measurement target, and corresponds to an average water content in the leaf contained in each pixel in the image capturing the leaf of the plant. The horizontal axis of the graph represents the elapsed time in days. Target range Bd as an example of the range of the target water content represents, for example, the range of water content determined to be suitable for increasing a sugar content of a fruit of a tomato, and here, a value corresponding to standardized pixel average water content index Dw is set to be a value in a range of 0.8 to 0.9. This target range Bd varies depending on the types of plants and even the same plants or the site of observation (leaves, stems, and the like). In addition, in FIG. 12 and FIG. 13, in a case where standardized pixel average water content index Dw is smaller than target range Bd, the plant feels water stress.

The first water potential control experiment as illustrated in FIG. 12 shows an example of time-transition (time-serial change) of the standardized pixel average water content index in a case where irrigation with nearly adequate irrigation amount is performed at irrigation timing. In FIG. 12, starting from a state where the leaf which is plant sample sm1 is wilted, the water potential control experiment is started after recovering by regular irrigation. In the regular irrigation, irrigation was periodically performed twice a day in the morning and evening in the day. On the other hand, in the water potential control experiment, the irrigation is performed at the timing determined to be appropriate based on the value of standardized pixel average water content index Dw, and periodical irrigation is not performed. Hereinafter, experiment results illustrated in FIG. 12 will be described. In addition, a temporal change of standardized pixel average water content index Dw as illustrated in FIG. 12 is displayed on monitor 50.

Standardized pixel average water content index Dw of the leaf begins with a wilting state close to the value 0.60 and normal irrigation is started (day 0). After the start of normal irrigation, the next day, standardized pixel average water content index Dw of the leaf recovered to the value close to 1.0. In addition, the normal irrigation was periodically (days 1 to 8) performed so that the value of standardized pixel average water content index Dw of the leaf was kept to be close to 1.0 for about a week. After that, water deprivation was performed for three days (days 9, 10, and 11). As a result of water deprivation, standardized pixel average water content index Dw of the leaf was gradually decreased and fell down to the value close to 0.7 (day 12).

As indicated by arrow r11 at current point, when a certain amount of irrigation is performed, standardized pixel average water content index Dw in the leaf rises and the peak thereof is temporarily included within target range Bw, then falls down based on the non-irrigation, and falls out of target range Bw. When the same certain amount of the irrigation is performed again at the timing indicated by arrow r12, standardized pixel average water content index Dw in the leaf rises again and the peak thereof is temporarily included in target range Bw, and thereafter, standardized pixel average water content index Dw in the leaf falls down based on the non-irrigation. At this time, standardized pixel average water content index Dw is lower than target range Bw, but the deviation amount thereof is smaller than that in the previous time. When the same certain amount of the irrigation is performed again at the timing indicated by arrow r13, the peak of standardized pixel average water content index Dw falls down after exceeding the upper limit value of target range Bw, but in this time, standardized pixel average water content index Dw is not lower than target range Bw. Furthermore, when the same certain amount of the irrigation is performed at the timing indicated by arrow r14, the peak of standardized pixel average water content index Dw falls down after exceeding the upper limit value of target range Bw, but standardized pixel average water content index Dw is mostly stayed in target range Bw (days 12 to 16).

Even though water deprivation occurred for the following two days (days 17 and 18), as indicated by arrows r15, r16, r17, and r18, similar irrigation was performed so that standardized pixel average water content index Dw in the leaf was controlled to be substantially within target range Bw.

Figure 13:
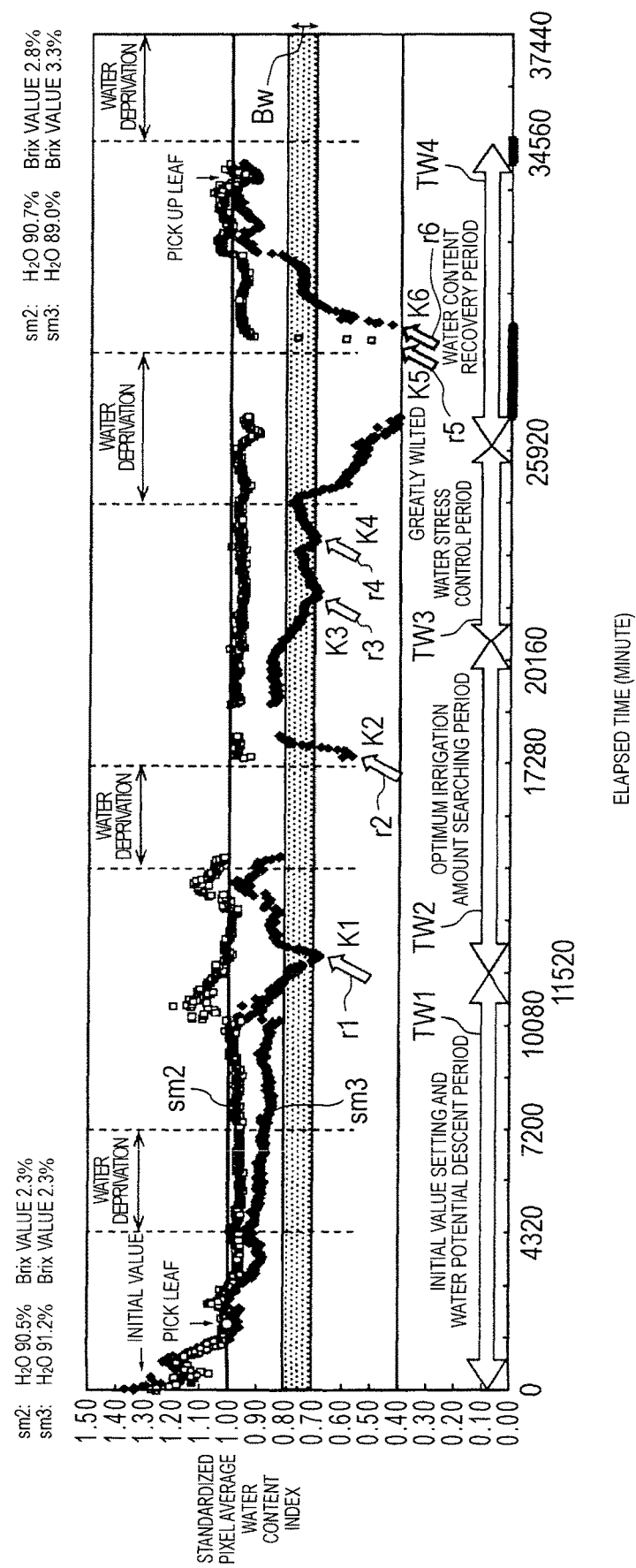
FIG. 13 is a graph illustrating an example of a time-transition of a standardized pixel average water content index in a second water potential control experiment.

FIG. 13 is a graph illustrating an example of a time-transition of standardized pixel average water content index Dw in the second water potential control experiment. The vertical axis of the graph indicates standardized pixel average water content index Dw, as illustrated in FIG. 12. The horizontal axis of the graph represents the elapsed time in minutes.

In the second water potential control experiment, two plant samples sm2 and sm3 (for example, tomatoes) of the same types, which are different from the first plant sample sm1, were used. For plant sample sm2 (Comparative Example), the normal irrigation is periodically performed twice a day in the morning and evening in the day. On the other hand, for plant sample sm3 (Example corresponding to the present embodiment), the irrigation is performed while applying the water stress. That is, for plant sample sm3, similar to the water potential control period (days 12 to 22) as illustrated in FIG. 12, the irrigation is only performed at the irrigation timing.

In the second water potential control experiment, as illustrated in FIG. 13, the observation of standardized pixel average water content index Dw in the leaf was performed during four periods of water potential descent period TW1, optimum irrigation amount searching period TW2, water stress control period TW3, and water content recovery period TW4. Target range Bw of standardized pixel average water content index Dw was different from target range Bw illustrated in FIG. 12, and was set to be a value in a range of in a range of 0.70 to 0.80. The reason for this is that the plant samples used in the second water potential control experiment were different from each other.

The initial values of the water content rate of the leaf in Comparative Example and Example are respectively 90.5% and 91.2%, which are almost the same each other. In addition, these standardized pixel average water content indexes Dw are close to the value of 1.30, which are almost the same each other. Further, the Brix values representing the sugar content of Comparative Example and Examples are the value of 2.3%, which are almost the same each other.

During the period of the control experiment of the water potential, the normal irrigation was continued for plant sample sm2 of Comparative Example.

On the other hand, the irrigation was not performed for plant sample sm3 of Example during water potential descent period TW1 (period from 0 to 11520 minutes) for plant sample sm3 of Example. As a result, since the initial value is set, standardized pixel average water content index Dw in the leaf of Comparative Example is nearly constant at the value close to 1.0; whereas standardized pixel average water content index Dw in the leaf of Example is gradually lowered, and is smaller than the value 0.70 which is the lower limit value of target range Bw at the end of water potential descent period TW1.

In optimum irrigation amount searching period TW2 (period from 11520 to 20160 minutes), firstly, standardized pixel average water content index Dw in the leaf of Example was smaller than the lower limit value of 0.70 of the target range so that the irrigation of irrigation amount K1 was performed at the time (timing) indicated by arrow r1. As a result, standardized pixel average water content index Dw in the leaf of Example rapidly rose, exceeded the upper limit value of target range Bw, and became the value close to 1.00. It is determined that irrigation amount K1 was excessively large at this point. After that, the water deprivation period began, and standardized pixel average water content index Dw in the leaf of Example was smaller than the lower limit value of the target range again so as to reach the value of 0.60. The water deprivation period is completed, irrigation of irrigation amount K2 was performed at the time indicated by arrow r2. As a result, standardized pixel average water content index Dw rose, and slightly exceeded target range Bw. Based on these results displayed on monitor 50, it can be determined that the optimum irrigation amount is less than irrigation amounts K1 and K2.

In water stress control period TW3 (period from 20160 to 25920), when standardized pixel average water content index Dw in the leaf of Example was decreased again, and was smaller than the lower limit value of target range Bw, the irrigation with irrigation amount K3 smaller than irrigation amounts K1 and K2 was performed at the time indicated by arrow r3. Also, standardized pixel average water content index Dw was smaller than the lower limit value of target range Bw, and at the time indicated by arrow r4, the irrigation was performed with irrigation amount K4 similar to irrigation amount K3. As described above, when the irrigation with irrigation amounts K3 and K4 is intermittently performed, standardized pixel average water content index Dw changes so as to be substantially within target range Bw while applying the water stress to plant sample sm3. Thereafter, since the leaf of plant sample sm3 of Example entered a certain water deprivation period, the degree of wilting of the leaf was increased, standardized pixel average water content index Dw was decreased, and thereby standardized pixel average water content index Dw of plant sample sm3 dropped to the value of 0.4.

The water deprivation period was completed, and in water content recovery period TW4 (period from 25920 to 34560), the degree of wilting of the leaf of plant sample sm3 was large, and thus the irrigation was performed with irrigation amounts K5 and K6 which are larger than irrigation amounts K3 and K4 at the time indicated by arrows r5 and r6.

At the end of water content recovery period TW4, when the rate of water content in the leaf of the plant samples sm2 and sm3 in Comparative Example and Example reached approximately the same values as the initial values (90.7%, 89.0%), as a result of measuring the Brix value representing each sugar content, the Brix value in Comparative Example was 2.8%; whereas in Example, the Brix value was 3.3%. That is, the Brix value of Comparative Example was increased by 0.5% from the value of 2.3% to 2.8% before and after the water potential control; whereas the Brix value of Example was greatly increased by 1% from the value of 2.3% to 3.3%.

In this way, compared to plant sample sm2 of Comparative Example in which the irrigation was performed at regular intervals without applying the water stress, in plant sample sm3 of Example, the irrigation was performed at the timing when standardized pixel average water content index Dw reached close to the lower limit of the target range while applying water stress based on non-irrigation so that an increase in the sugar content in the leaf was increased, and the sugar content in the leaf was increased due to the water stress. In this way, it was found that the leaf quality was increased by applying the water stress through the water potential control experiment in FIG. 13.

Here, the sugar content in the leaf was measured in the following procedures (T1) to (T5).

(T1) A leaf such as a tomato is dried at temperature of 105° C. for two hours. From this change in weight, the water content can be calculated.

(T2) The dried leaf is put into a mortar, and is crushed and ground to be in a powder state.

(T3) The powder obtained by crushing the leaf is put into a container containing hot water at 60° C. which has four times water content (before drying) contained in the leaf, and stir at room temperature for 2 hours.

(T4) The container containing the leaf powder is left to stand, and the leaf powder is allowed to be settled spontaneously for 15 hours or more.

(T5) A supernatant was extracted and the Brix value thereof was measured by using a sugar content meter.

Here, since this Brix value is a provisional Brix value obtained using hot water four times the water content in the leaf, a true Brix value can be obtained according to Expression (1). Note that, the calculation of the true Brix value by Expression (1) may be performed by controller 11 when the Brix value obtained by the sugar content meter is input.

$$\text{True Brix value (\%)} = [\text{provisional Brix value} \times \text{water content} \times 4 \text{ times}/(1 - \text{provisional Brix value})] \div [\text{water content} + (\text{provisional Brix value} \times \text{water content} \times 4 \text{ times})/(1 - \text{provisional Brix value})] \times 100 \quad (1)$$

Figure 14:
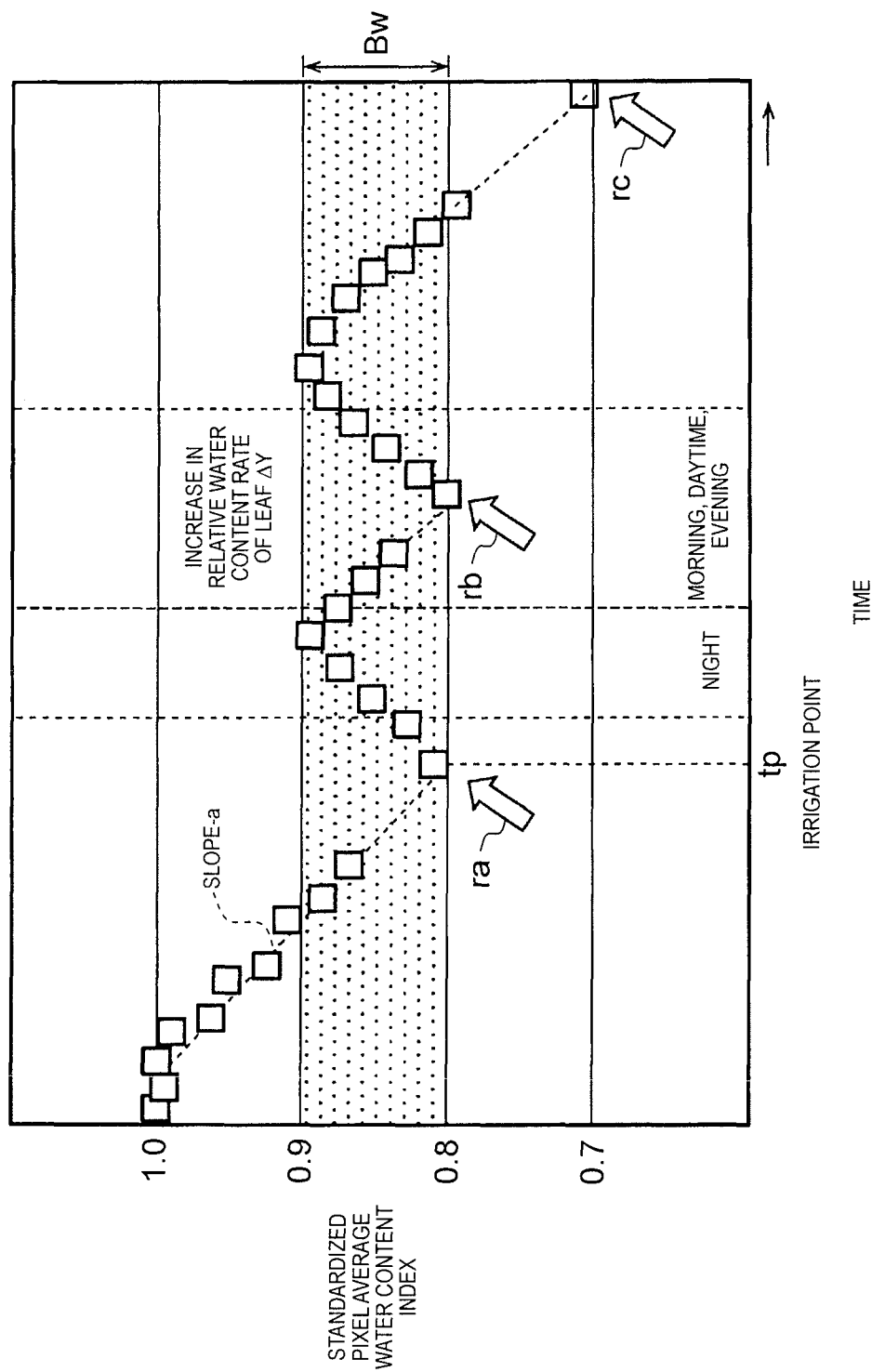
FIG. 14 is a graph illustrating an example of an irrigation amount and irrigation timing.

On the basis of the control experiment of the water potential, the following irrigation amount and irrigation timing are considered. FIG. 14 is a graph illustrating an example of an irrigation amount and irrigation timing. The vertical axis of the graph indicates a standardized water content index (that is, standardized pixel average water content index Dw). The horizontal axis represents elapsed time. In the graph, a measurement point is represented by a rectangle. Target range Bw is set to be a value in a range of 0.8 to 0.9.

An initial value of standardized pixel average water content index Dw in the leaf is set a value of 1.0. When standardized pixel average water content index Dw is gradually decreased with the lapse of time from the initial value and reaches close to the lower limit value of target range Bw, the following irrigation is performed. When a slope (descending speed) at which standardized pixel average water content index Dw is decreased is "−a", the timing indicated by arrow ra at which standardized pixel average water content index Dw crosses the lower limit value of target range Bw is irrigation point tp.

Irrigation amount Kp in irrigation point tp is calculated by using, for example, Expression (2).

$$\text{Next water content in leaf} = \text{present water content in leaf} + \text{amount of water absorption from root} - \text{amount of transpiration from leaf} \quad (2)$$

Here, the amount of water absorption from the root is calculated by the irrigation amount, osmotic pressure (electric conductivity) of a liquid fertilizer, the number (surface area) of roots, and the like. The amount of transpiration from the leaf is obtained from the number of leaves, a leaf area, saturation deficit (that is, a difference between saturated water vapor pressure and relative humidity), and the like. Generally, it is said that photosynthesis of a leaf is active and the transpiration is actively performed on a sunny day and when the saturation deficit is between 3 to 7 g/m$^3$ (that is, the period in which the relative humidity is around 75% RH). Therefore, the water content in the leaf tends to be decreased due to the transpiration in the morning and daytime on a sunny day; whereas in the evening (sunset), when the amount of transpiration of the leaf is decreased, the water content in the leaf is increased. In addition, the leaf is not subjected to the photosynthesis at night, and thus the change in the water content in the leaf is small. Since the relative humidity is high on a rainy day, the transpiration is not performed even if the pore is opened, and thus the change in the water content in the leaf is small, and on the day when the temperature is high such as summer, the plant closes the pores so as not to lose the water in the body any more so that the transpiration is not performed, and thereby the change in the water content in the leaf is small.

When the irrigation is performed, standardized pixel average water content index Dw rises, reaches the upper limit value of target range Bw, and then repeats a fallingdown operation. At the timing indicated by arrow rb, the same irrigation as that at the timing indicated by arrow ra is performed. Thereafter, at the timing indicated by arrow rc, the irrigation is performed at the timing when standardized pixel average water content index Dw reaches the value 0.7, which is lower than the lower limit value of target range Bw, that is, in a state where the water stress is increased. This makes it possible to apply the water stress to the plant.

Figure 15:
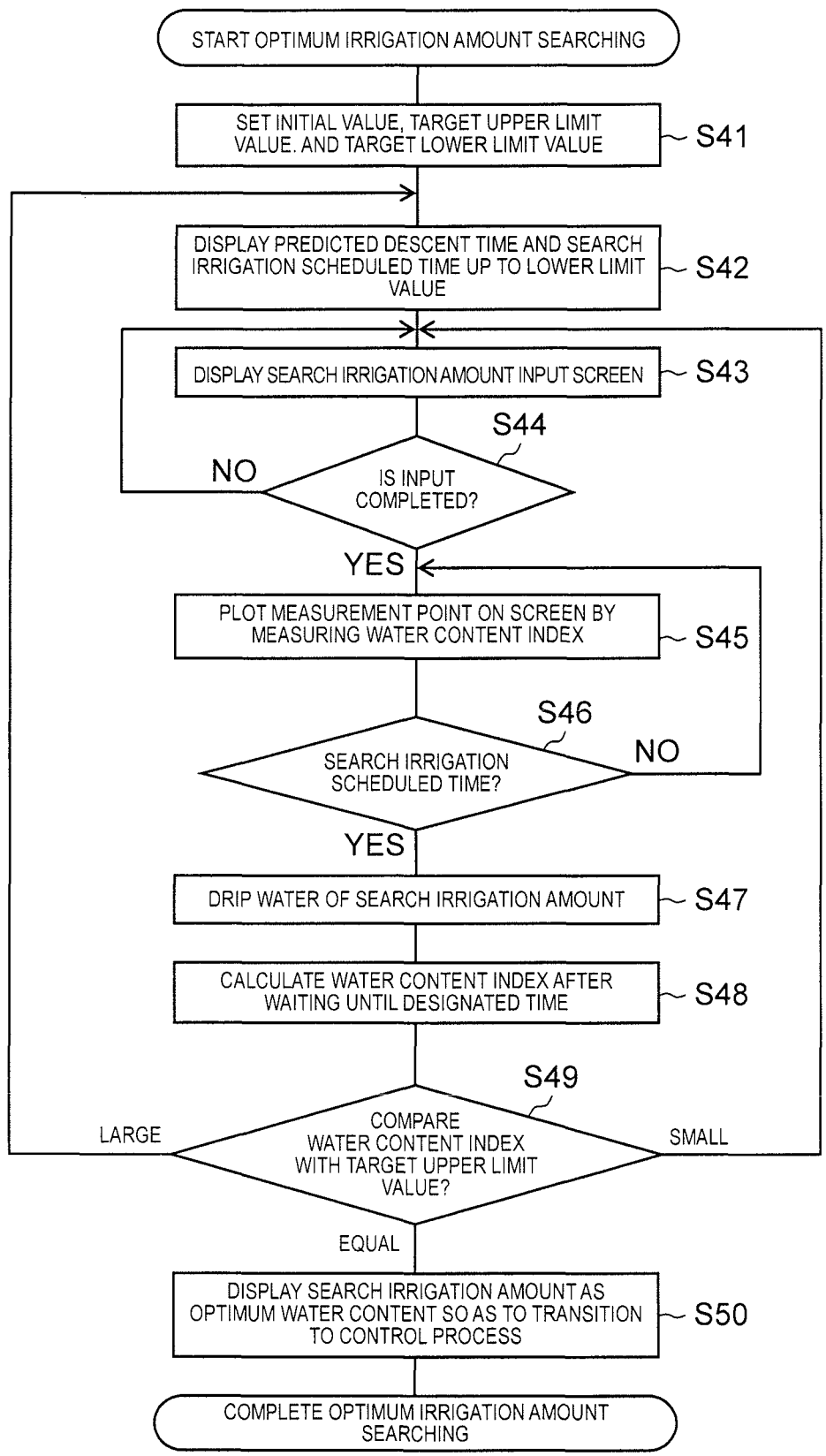
FIG. 15 is a flow chart illustrating an example of searching procedure of the optimum irrigation amount in the first embodiment.
Figure 16:
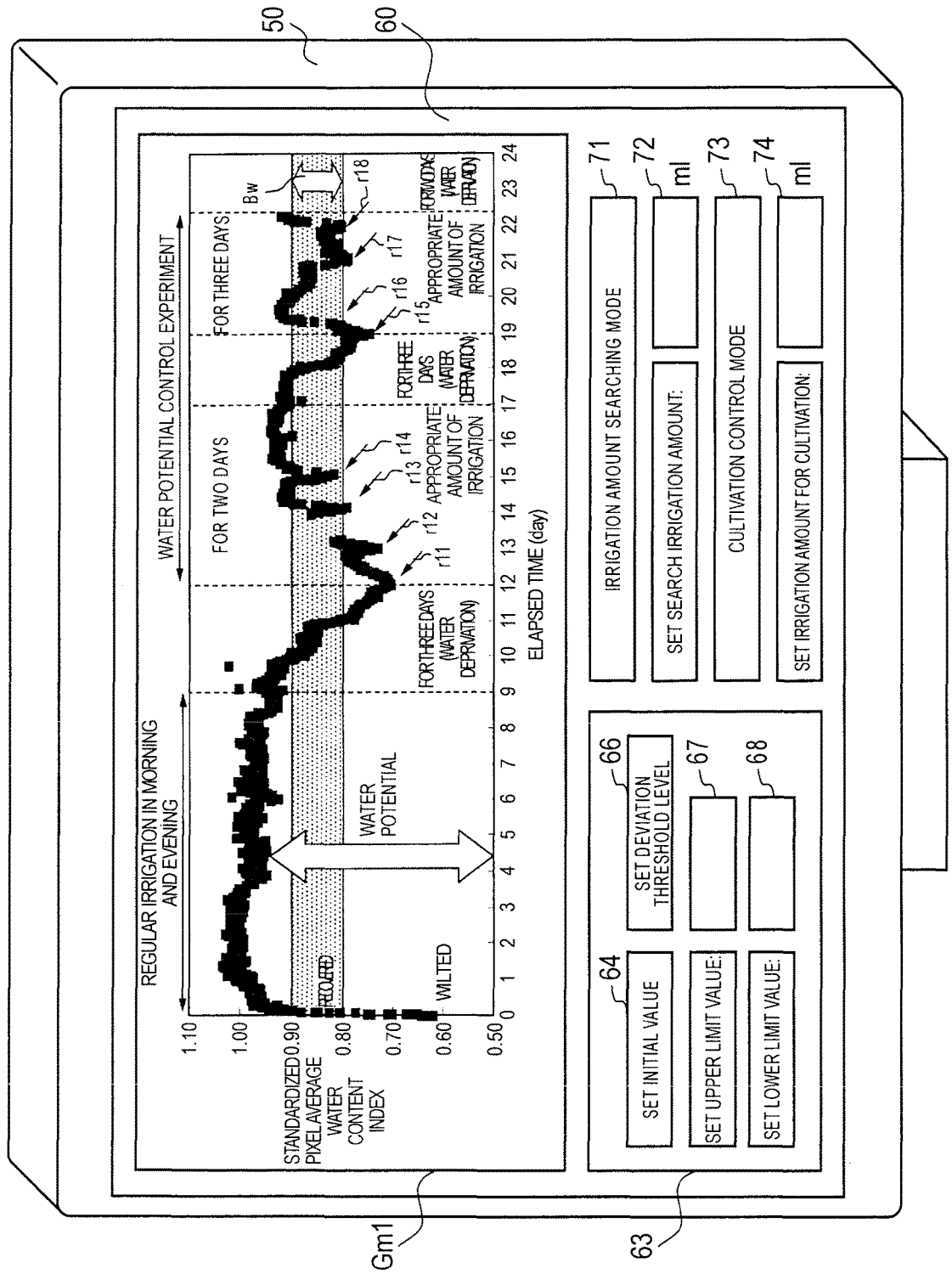
FIG. 16 is a diagram illustrating an example of a user interface (UI) screen relating to water potential control.

FIG. 15 is a flow chart illustrating an example of searching procedure of the optimum irrigation amount in the first embodiment. This optimum irrigation amount searching operation is a process executed in optimum irrigation amount searching period TW2 as illustrated in FIG. 13. For example, when irrigation amount searching mode button 71 is pressed on UI screen 60 as illustrated in FIG. 16, the optimum irrigation amount searching operation is executed.

In the optimum irrigation amount searching operation, first, controller 11 sets an initial value, and the upper limit value and the lower limit value of target range Bw by the operation of a user (for example, a farmer of tomatoes who is a user) with respect to UI screen 60 (S41). Controller 11 displays a predicted descent time and a search irrigation scheduled time up to the lower limit value of target range Bw (S42). Note that, this search irrigation scheduled time is set to be the same as or near the predicted descent time.

Figure 17:
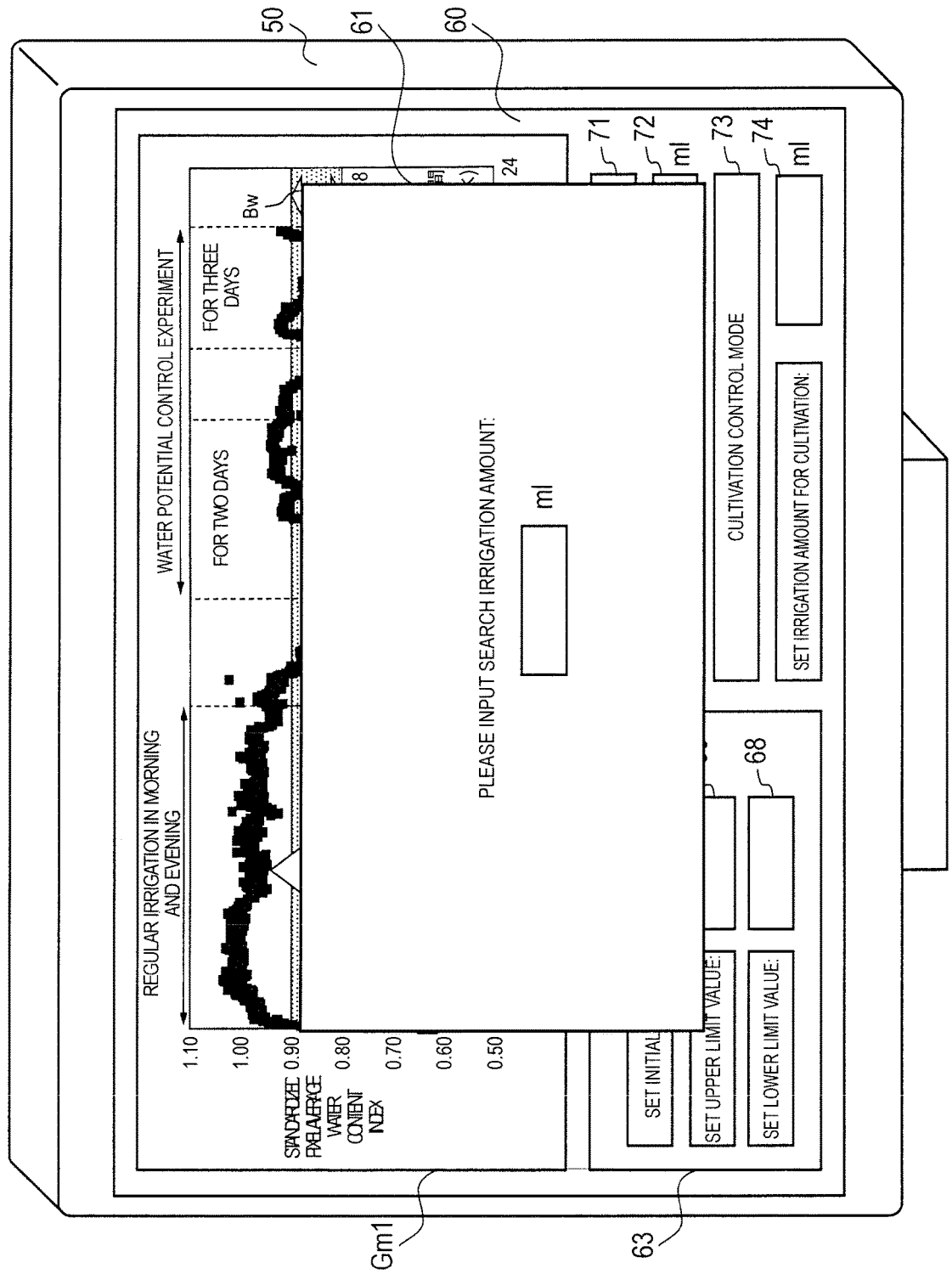
FIG. 17 is a diagram illustrating an example of a search irrigation amount input screen pop-up displayed on a UI screen.

Controller 11 displays search irrigation amount input screen 61 illustrated in FIG. 17 (S43). Controller 11 determines whether or not the input of the search irrigation amount has been completed (S44), and if the input is not completed, controller 11 continues to display search irrigation amount input screen 61 in step S43.

In addition, when the input of the search irrigation amount is completed, controller 11 measures standardized pixel average water content index Dw, and adds this measurement point to the graph in screen for monitoring water content in leaf Gm1 which is displayed on UI screen 60 (S45). Controller 11 determines whether or not search irrigation scheduled time has come (S46). In a case where the search irrigation scheduled time has come, controller 11 returns to the process of step S45.

When the search irrigation scheduled time has come, controller 11 controls the dripping of the search irrigation amount (S47). The search irrigation amount corresponds to irrigation amounts K1 and K2 in FIG. 13. In addition, the dripping of the moisture of the search irrigation amount may be automatically performed by fertilizer or water supply device WF, or may be performed manually by a user. After waiting until the designated time, controller 11 calculates the water content index (S48). This designated time is a time designated so that standardized pixel average water content index Dw reaches the upper limit value of target range Bw, and is set based on the predicted descent time and the search irrigation scheduled time.

Controller 11 compares standardized pixel average water content index Dw with the upper limit value of target range Bw (S49). In a case where standardized pixel average water content index Dw exceeds the upper limit value of target range Bw, controller 11 returns to step S42, and displays the predicted descent time and the search irrigation scheduled time on UI screen 60 again. In addition, in a case where standardized pixel average water content index Dw does not exceed the upper limit value of target range Bw, controller 11 returns to step S43, and displays search irrigation amount input screen 61.

Further, in a case where standardized pixel average water content index Dw becomes equal to the upper limit value of target range Bw, controller 11 displays the search irrigation amount as an optimum water content so as to change to the process of the cultivation control (S50). This display is pop-up displayed, for example, by a message or the like. Thereafter, controller 11 completes the present operation.

FIG. 16 is a diagram illustrating an example of a user interface (UI) screen 60 relating to water potential control. UI screen 60 includes screen for monitoring water content in leaf Gm1. A graph representing a time-transition of standardized pixel average water content index Dw is displayed on screen for monitoring water content in leaf Gm1 disposed on the upper portion of UI screen 60. This graph is similar to the graph of FIG. 12 described above.

Set area 63 is displayed on the left side of the lower portion of UI screen 60. Initial setting button 64 and deviation threshold level setting button 66 are disposed in set area 63. In addition, input box 67 for setting the upper limit value of target range Bw and input box 68 for inputting the lower limit value of target range Bw are disposed. For inputting numerical values to input boxes 67 and 68, it is possible to use a touch panel, a numeric keypad, a portable terminal, or the like.

Figure 18:
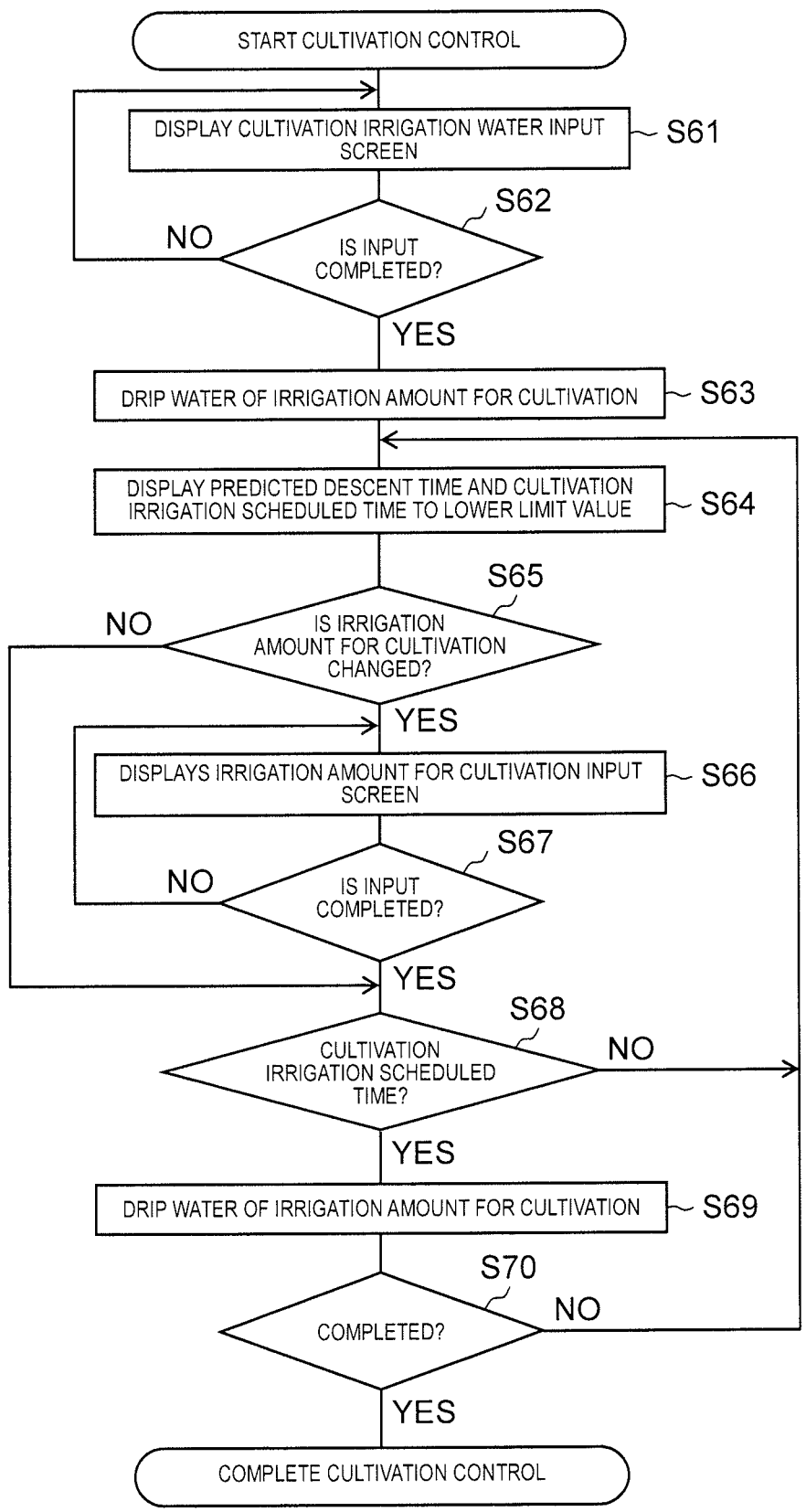
FIG. 18 is a flow chart illustrating an example of procedure of water stress control (cultivation control) of the first embodiment.

In addition, irrigation amount searching mode button 71 and water stress control. (cultivation control) mode button 73 are disposed on the right side of the lower portion of UI screen 60. When irrigation amount searching mode button 71 is pressed, the optimum irrigation amount searching operation as illustrated in FIG. 15 is started. When water stress control (cultivation control) mode button 73 is pressed, the cultivation control operation as illustrated in FIG. 18 to be described later is started. Further, on UI screen 60, display box 72 for displaying a setting value of the search irrigation amount and display box 74 for displaying a setting value of the irrigation amount for cultivation are disposed.

FIG. 17 is a diagram illustrating an example of search irrigation amount input screen 61 pop-up displayed on UI screen 60. In search irrigation amount input screen 61, the search irrigation amount is input and set by unit of milliliter (ml). A touch panel, a numeric keypad, a mobile terminal, and the like can be used for inputting the search irrigation amount.

FIG. 18 is a flow chart illustrating an example of procedure of water stress control (cultivation control) of the first embodiment. This cultivation control operation is a process executed in water stress control period TW3 as illustrated in FIG. 13. For example, when water stress control (cultivation control) mode button 73 is pressed on UI screen 60 as illustrated in FIG. 16, the cultivation control operation is executed.

In the water stress control operation, controller 11 firstly displays a cultivation (control) irrigation amount input screen (S61). The input screen of irrigation amount for cultivation is pop-up displayed on UI screen 60 similar to the search irrigation amount input screen.

Controller 11 determines whether or not the input of the irrigation amount for cultivation is completed on the input screen of irrigation amount for cultivation (S62). The irrigation amount for cultivation represents the appropriate irrigation amount calculated in the searching process of optimum irrigation amount searching period TW2 (that is, the flow chart as illustrated in FIG. 15). In a case where the input of the irrigation amount for cultivation is not completed, controller 11 returns to step S61 and continues to display the input screen of irrigation amount for cultivation.

On the other hand, when the input of the irrigation amount for cultivation is completed, controller 11 drips the water of the irrigation amount for cultivation (S63). Controller 11 displays the predicted descent time and the cultivation irrigation scheduled time up to the lower limit value of target range Bw (S64). Note that, this cultivation irrigation scheduled time is set to be the same as or near the predicted descent time.

Controller 11 determines whether or not the irrigation amount for cultivation is changed (S65). In a case where the irrigation amount for cultivation is not changed, controller 11 proceeds to the process of step S68. On the other hand, in a case where the irrigation amount for cultivation is changed, controller 11 displays the input screen of irrigation amount for cultivation again (S66). Controller 11 determines whether or not the input of the irrigation amount for cultivation is completed on the input screen of irrigation amount for cultivation (S67). In the case where the input of the irrigation amount for cultivation is not completed, controller 11 returns to step S66 and continues to display the input screen of irrigation amount for cultivation.

On the other hand, when the input of the irrigation amount for cultivation is completed, controller 11 determines whether or not the cultivation irrigation scheduled time has come (S68). In a case where the cultivation irrigation scheduled time has not come yet, controller 11 returns to the process of step S64. When the cultivation irrigation scheduled time has come, controller 11 drips the water of the irrigation amount for cultivation (S69). Controller 11 determines whether or not the cultivation control is completed (S70). In a case where the cultivation control is not completed, controller 11 returns to the process of step S64. On the other hand, in the case where the cultivation control is completed, controller 11 completes the present operation.

Next, a water stress profile for applying the water stress to the plant will be described. FIG. 19A to FIG. 19D are graphs schematically illustrating an example of the water stress profile. In water stress profile pf1 as illustrated in FIG. 19A, the irrigation is performed such that the water content index (that is, standardized pixel average water content index Dw) is fluctuated between the upper limit value and the limit value target range Bw (the range of the target water content). That is, the irrigation with the irrigation amount which reaches the upper limit value of target range Bw is performed at the timing of the lower limit value of target range Bw. In this case, the water stress is small.

Figure 19B:
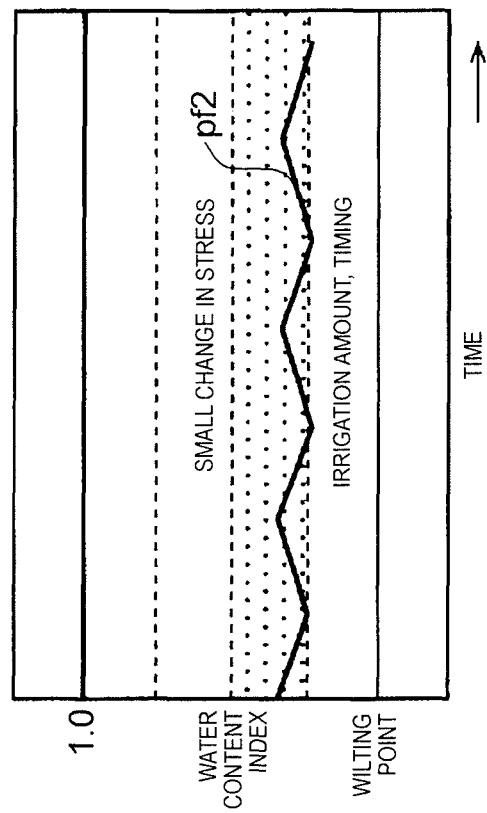
FIG. 19B is a graph schematically illustrating an example of a water stress profile.

In water stress profile pf2 as illustrated in FIG. 19B, the irrigation is performed by the lower limit value of target range Bw, and the peak of standardized pixel average water content index Dw falls in the middle of target range Bw such that the fluctuation of standardized pixel average water content index Dw is reduced. In this case, the water stress is slightly small.

Figure 19D:
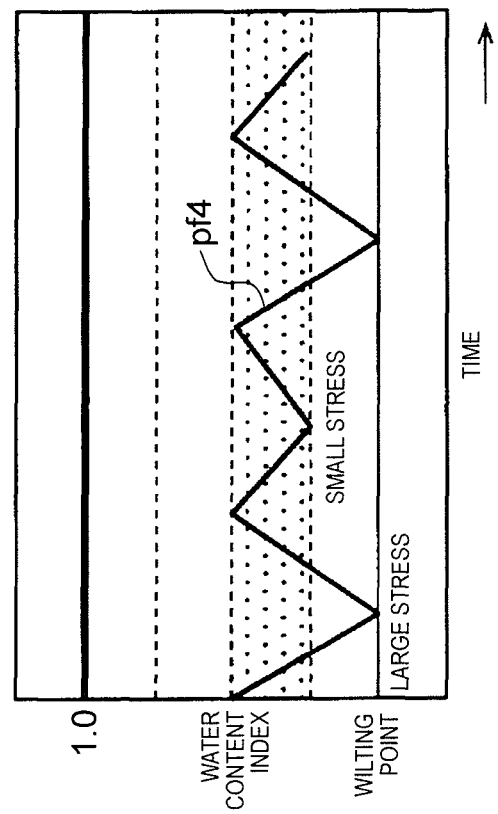
FIG. 19D is a graph schematically illustrating an example of a water stress profile.
Figure 19A:
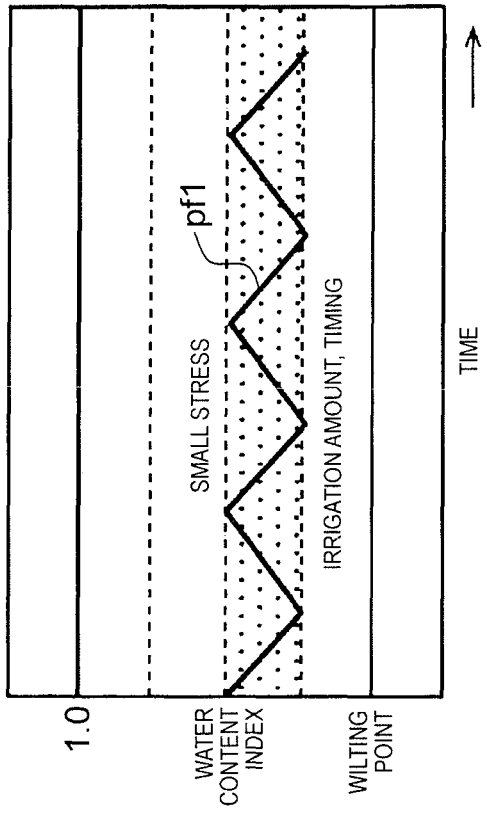
FIG. 19A is a graph schematically illustrating an example of a water stress profile.
Figure 19C:
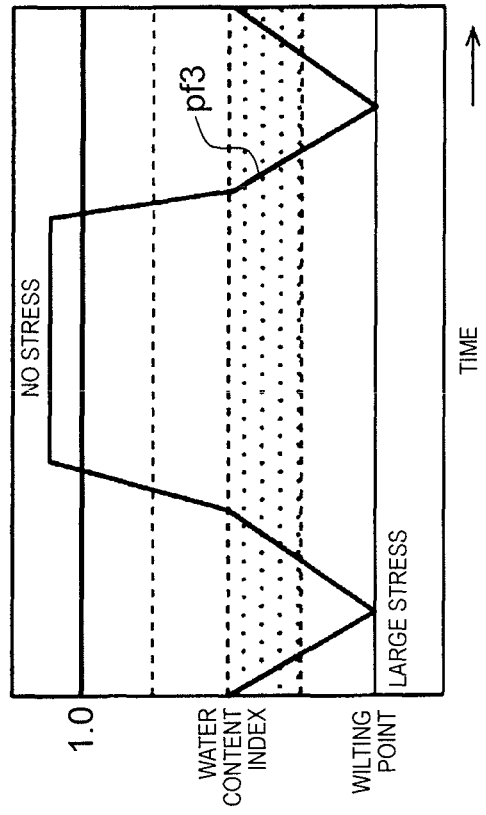
FIG. 19C is a graph schematically illustrating an example of a water stress profile.

In water stress profile pf3 as illustrated in FIG. 19C, after standardized pixel average water content index Dw falls down to an wilting point, the irrigation is performed with a large amount of irrigation, and after standardized pixel average water content index Dw rises until it exceeds the value of 1, it falls down again to the wilting point, and the irrigation is performed in the same manner. In this case, there is no water stress in an area where standardized pixel average water content index Dw exceeds the value of 1, and the water stress is large in the vicinity of the wilting point. This water stress profile pf3 is used, for example, in a case where the water content index is changed at flowering and fruiting season of the plant in another stage or the weather is changed.

In water stress profile pf4 as illustrated in FIG. 19D, after standardized pixel average water content index Dw falls down to the wilting point, the irrigation is performed with the irrigation amount that reaches the upper limit value of target range Bw, and when standardized pixel average water content index Dw reached the upper limit value of target range Bw, and then reaches the lower limit value of target range Bw again, the irrigation with the irrigation amount that reaches the upper limit value of target range Bw is performed.

Such operations are alternately repeated. In this case, when standardized pixel average water content index Dw is in the vicinity of the wilting point, the water stress becomes larger, and when standardized pixel average water content index Dw is in the vicinity of the lower limit value of target range Bw, the water stress becomes smaller. Note that, these water stress profiles are an example, and other water stress profiles can be applied.

As described above, in plant detection camera 1 according to the first embodiment, first beam source 13 of plant detection camera 1 performs optical scanning so that the near infrared beam (reference beam) of the first wavelength (905 nm), which has a characteristic in which light tends not to be absorbed in water is radiated toward leaf PT3 of plant PT. Second beam source 15 of plant detection camera 1 performs optical scanning so that the near infrared beam (reference beam) of the second wavelength (1550 nm), which has a characteristic easily absorbed by water is radiated toward leaf PT3 of plant PT. Threshold level setter/water content index detector 27a calculates a total sum of the water content index of one leaf, which is the total sum of the reflection intensity ratio an $\Sigma$ Ln ($I_{905}/I_{1550}$), and the pixel average water content index based on the reflection light of 905 nm reflected on the entire irradiation position of leaf PT3 and the reflection light of 1550 nm reflected on the entire irradiation position of leaf PT3. Controller 11 displays a graph representing the time-transition of the water content contained in leaf PT3 of plant PT from the start to the end of the measurement period on UI screen 60 of monitor 50. When viewed from first beam source 13 and second beam source 15, white reference substrate bd (background material) which covers a back surface of leaf PT3 of plant PT is disposed on leaf PT3 of plant PT.

As such, according to plant detection camera 1, it is possible to quantitatively and time-serially suggest the change of the water content contained in the plant by displaying the graph representing the time-transition of the water content contained in leaf PT3 of plant PT on UI screen 60 of monitor 50. In addition, according to the time-transition of standardized pixel average water content index Dw contained in leaf PT3 displayed on UI screen 60 of monitor 50, plant detection camera 1 can teach the user the timing of the irrigation to leaf PT3 and the irrigation amount. The user can perform the irrigation with an appropriate irrigation amount at an appropriate irrigation timing from the graph displayed on UI screen 60 of monitor 50. Accordingly, it is possible to perform optimum cultivation control when realizing a function of the plant such as a tomato so that yield can be improved and productivity can be enhanced.

Further, according to plant detection camera 1, target range Bw of standardized pixel average water content index Dw (water content) of the plant, an initial value of the water content, and the change of the water content fell down due to the non-irrigation as an example of the application of the stress (for example, water stress) are displayed, and thus the user can grasp the water content of the plant in time series.

In addition, according to plant detection camera 1, it is possible to search the optimum irrigation amount such that standardized pixel average water content index Dw (water content) of the plant is included within target range Bw.

Further, according to plant detection camera 1, both of falling down of the water content by the non-irrigation as an example of application of the stress (for example, water stress) and rising of the water content by the irrigation are displayed, and thus the optimum irrigation amount can be more easily searched such that standardized pixel average water content index Dw is included within target range Bw.

In addition, according to plant detection camera 1, target range Bw of the water content of the plant and the change of the water content by the irrigation for maintaining the water content of the plant within the target range are displayed, and thus the irrigation with the irrigation amount can be easily performed such that the water content of the plant is included within the target range.

Further, according to plant detection camera 1, the water content contained in the plant for which the irrigation is performed by the normal irrigation, and the water content contained in the plant for which the irrigation is performed while applying the water stress are relatively compared to each other, and thus the user can efficiently and highly accurately determine appropriateness of the irrigation amount and the irrigation timing.

Modification Example 1 of First Embodiment

Figure 20:
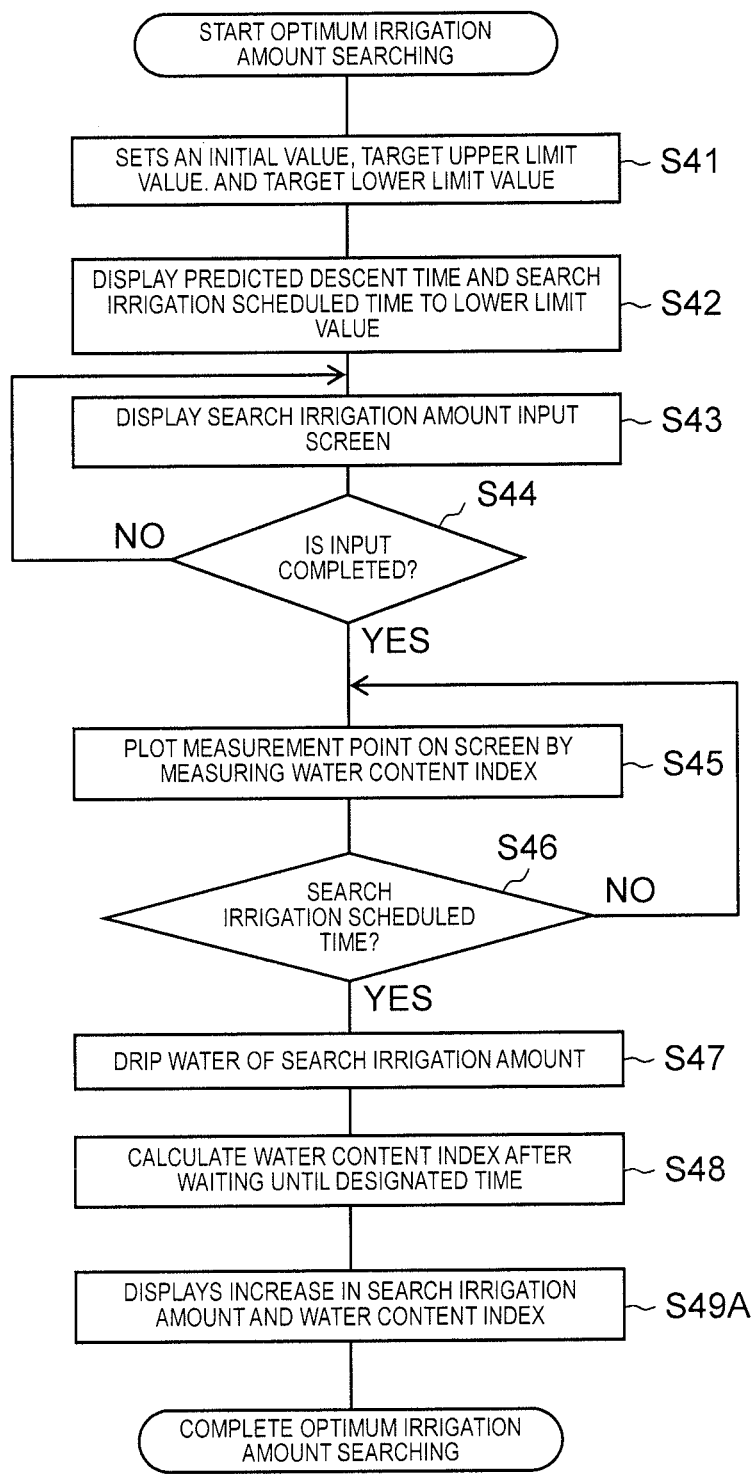
FIG. 20 is a flow chart illustrating an example of searching procedure of the optimum irrigation amount in Modification Example 1 of the first embodiment.

FIG. 20 is a flow chart illustrating an example of searching procedure of the optimum irrigation amount in Modification Example 1 of the first embodiment. The same step processing as in FIG. 15 is denoted by the same step number, and the description thereof will not be repeated. After waiting until the designated time in step S48, controller 11 calculates the water content index, and then displays the search irrigation amount and the increase in standardized pixel average water content index Dw so as to maintain the water content index within target range Bw (within the range) (S49A). Based on these displays, the user can infer the optimum water content. Thereafter, controller 11 completes the present operation.

Second Embodiment

The second embodiment describes a case where positional deviation of leaves occurs due to some influences during the continuous measurement of standardized pixel average water content index Dw in the leaf. In a case where a white reference substrate to which the leaf that is a measurement target is attached tilts due to, for example, strong wind and collision, and the positional deviation of the leaves occurs during the measurement of standardized pixel average water content index Dw in the leaf in time series, standardized pixel average water content index Dw in the leaf measured by the reflection intensity ratio due to the irradiation of the laser beam is rapidly changed.

In a case where the positional deviation of the leaf that is a measurement target occurs, data in which standardized pixel average water content index Dw in the leaf is recorded in time series is fluctuated at once, and the continuity thereof is lost, and thus, in the related art, data of standardized pixel average water content index Dw measured in time series so far is discarded, and the measurement is started again from the beginning. As a result, the acquisition efficiency of measurement data remarkably decreased.

In the second embodiment, even in a case where the positional deviation of the leaves occurs, by effectively utilizing the data measured in time series so far without discarding, the data of standardized pixel average water content index Dw in the leaf can be efficiently acquired and the increase of measurement time is suppressed.

Figure 21A:
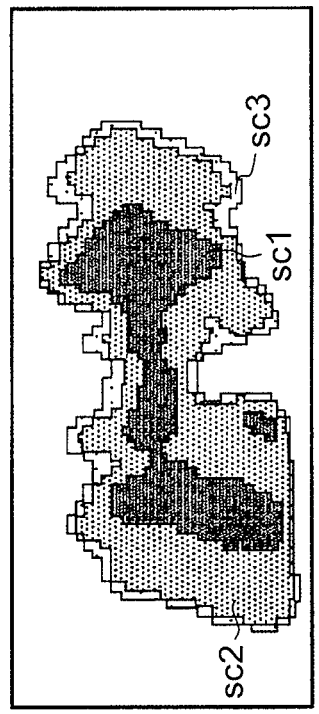
FIG. 21A is a diagram illustrating an example of an image indicating a water content in a leaf that is a measurement target, which is captured by a plant detection camera of the second embodiment, and an example of an image of a leaf before positional deviation.
Figure 21B:
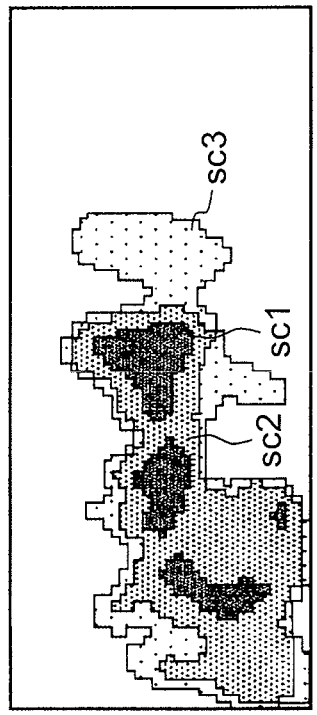
FIG. 21B is a diagram illustrating an example of an image indicating a water content in a leaf that is a measurement target, which is captured by a plant detection camera of the second embodiment, and an example of an image of a leaf after positional deviation.

FIG. 21A is a diagram illustrating an example of an image indicating a water content in a leaf that is a measurement target, which is captured by plant detection camera 1 of the second embodiment, and an example of an image of a leaf before positional deviation. FIG. 21B is a diagram illustrating an example of an image indicating a water content in a leaf that is a measurement target, which is captured by plant detection camera 1 of the second embodiment, and an example of an image of a leaf after positional deviation. In the drawings, an area which is dark and has a large number of dots is an area having a large water content. Area sc1 which is a darkest area (with the largest water content) exists inside the leaf. Area sc2 which is the next darkest area (with slightly large water content) exists around area sc1. Area sc3 which is a light area (with small water content) exists outside the leaf. In addition, compared with before the positional deviation, the size of area sc1 having a large water content is increased after the positional deviation.

Figure 22:
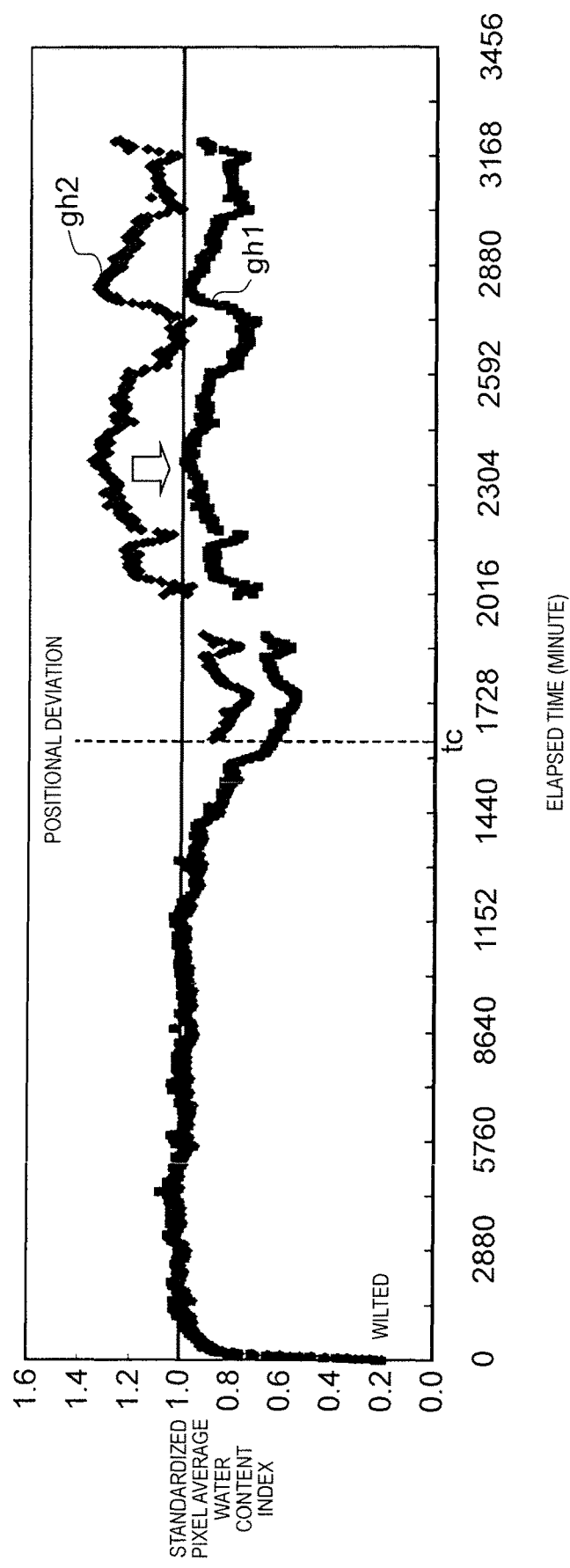
FIG. 22 is a graph illustrating an example of a time-transition of a standardized pixel average water content index in a water potential control experiment in a case where the positional deviation occurs.

FIG. 22 is a graph illustrating an example of a time-transition of standardized pixel average water content index Dw in the water potential control experiment in a case where the positional deviation occurs. This vertical axis of the graph indicates the standardized pixel average water content index similar to the first embodiment. The standardized pixel average water content index represents the water potential and represents a value corresponding to the water content contained per pixel in an image of the leaf of the plant. The horizontal axis of the graph represents the elapsed time in minutes.

When the positional deviation of leaves (refer to timing tc in the drawings) occurs, standardized pixel average water content index Dw is changed at once. Standardized pixel average water content index Dw in the leaf in a case where the positional deviation of leaves does not occur is changed as illustrated in graph gh1. On the other hand, standardized pixel average water content index Dw in the leaf in the case where the positional deviation of leaves occurs is changed as illustrated in graph gh2.

In the second embodiment, even in the case where the positional deviation of the leaves occurs, by performing the correction based on the following consideration, the data of standardized pixel average water content index Dw before the positional deviation of the leaves is effectively utilized, and the data of standardized pixel average water content index Dw in time series is acquired so as to maintain the continuity with the data of standardized pixel average water content index Dw after the positional deviation of the leaves.

In the following consideration, it is assumed that leaves are tilted as the positional deviation of the leaves. In this case, changing an angle as the leaves are tilted in a pan direction or a tilt direction corresponds to changing the thickness of the leaf as seen from the camera.

The water content (in other words, water potential) in the leaf is water amount contained in the leaf is proportional to standardized pixel average water content index Dw.

Further, as described above, standardized pixel average water content index Dw is calculated by summing the reflection intensity ratio Ln ($I_{905}/I_{1550}$) and the number of pixels occupying green (G) out of the number of pixels constituting the invisible light image of the leaf or the number of pixels constituting the visible light captured image of the leaf.

It is known that the reflection intensity ratio Ln ($I_{905}/I_{1550}$) is substantially proportional to (correlated with) leaf thickness t, as represented by Expression (3) based on known Lambert Beer's law. In Expression (3), a is an absorption coefficient of water, t is a leaf thickness, C is water concentration, and β is a scattering loss term.

$$Ln(I_{905}/I_{1550})=\alpha \cdot t \cdot C+\beta \quad (3)$$

In summary, the water content (water potential) in the leaf is represented by a linear function of standardized pixel average water content index Dw having leaf thickness t as a gradient (slope). That is, the slope of the water content in the leaf is changed with leaf thickness t.

As described above, from the fact that the change in the angle of the leaf due to the positional deviation corresponds to the change in the slope due to leaf thickness t, it is possible to obtain the data of standardized pixel average water content index Dw before the positional deviation by multiplying coefficient Q (correction coefficient) corresponding to the change (the change in the slope due to the leaf thickness t) in the leaf angle by the data of standardized pixel average water content index Dw after the positional deviation.

As a result, the data of standardized pixel average water content index Dw obtained in time series before and after the positional deviation can maintain the continuity. Here, since the acquisition of the water content immediately before and after the positional deviation is performed within a short time, the substantial water content is not changed between before and after the positional deviation.

In detail, a correction example of standardized pixel average water content index Dw before and after the positional deviation will be described. FIG. 23 is a diagram illustrating a table indicating an example of the standardized pixel average water content index before and after positional deviation correction in time series.

In this table, in the graph illustrated in FIG. 22, in a case where the positional deviation occurs at the elapsed time of 16250 minutes (time 17:10), standardized pixel average water content index Dw before correction and standardized pixel average water content index Dw after correction are indicated. Here, coefficient Q corresponding to the change in the angle of the leaf is calculated by controller 11 as an example of the coefficient calculation unit, and specifically, the value is 0.7303 (=0.6416/0.8785).

Figure 24:
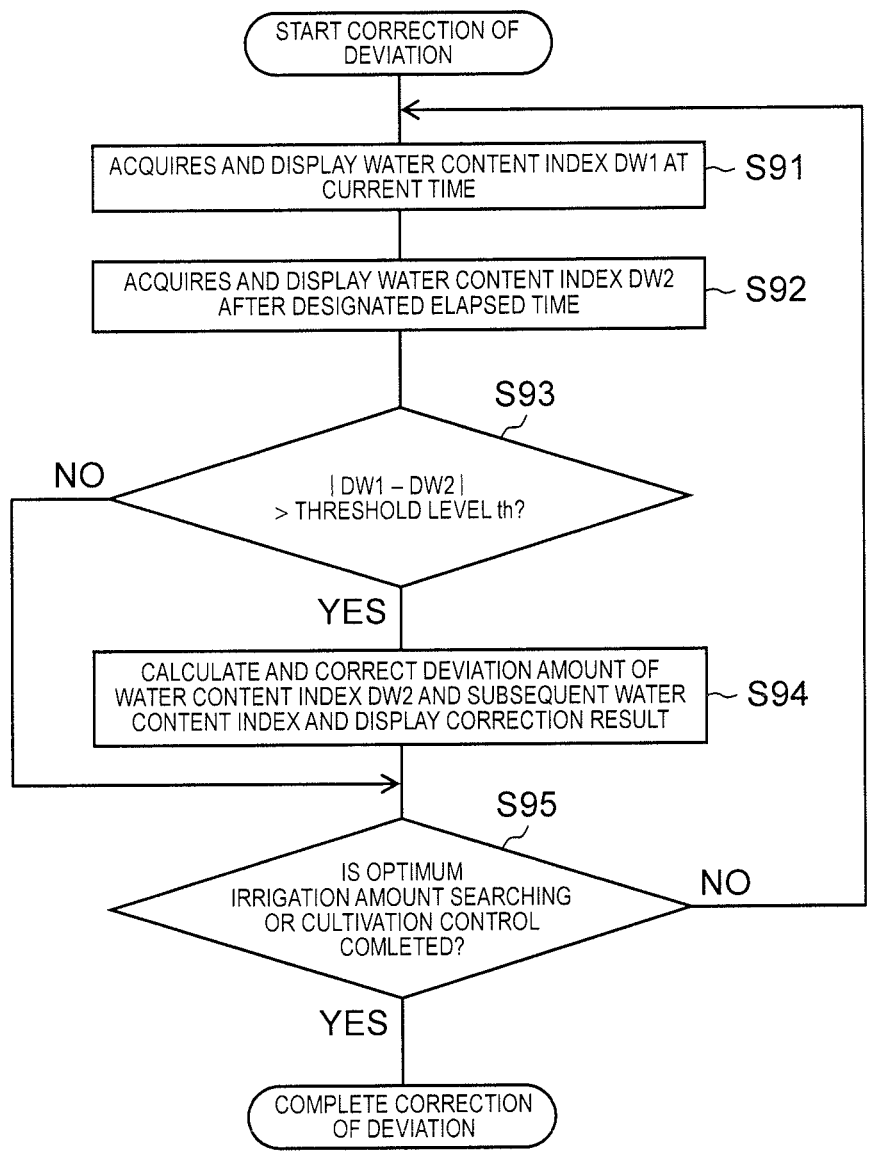
FIG. 24 is a flow chart illustrating an example of correction procedure of the positional deviation of second embodiment.

FIG. 24 is a flow chart illustrating an example of correction procedure of the positional deviation of second embodiment. Plant detection camera 1 of the second embodiment has substantially the same configuration as that of the first embodiment. The same reference numerals are used for the same constituent elements as those of the first embodiment, and a description thereof will not be repeated.

Controller 11 acquires and displays standardized pixel average water content index Dw1 at a current time on UI screen 60 (S91). Controller 11 acquires and displays standardized pixel average water content index Dw2 after designated elapsed time (for example, after 30 minutes) (S92). The designated elapsed time corresponds to a measurement interval.

Controller 11 determines whether or not the difference between standardized pixel average water content index Dw1 and standardized pixel average water content index Dw2 exceeds threshold level th (S93). This threshold level th is used for the determination of the value which is assumed to change standardized pixel average water content index Dw due to the positional deviation of the leaves.

Here, threshold level th is set in advance. At the time of setting threshold level th, controller 11 displays a deviation determining threshold level input screen. The user inputs threshold level th to the deviation determining threshold level input screen in order to determine that the positional deviation occurs. When the input is completed, controller 11 displays this input value and accepts the setting of threshold level th.

In a case where the difference between standardized pixel average water content index Dw1 and standardized pixel average water content index Dw2 does not exceed threshold level th, that is, in a case where it is assumed that the positional deviation of the leaves does not occur, controller 11 proceeds the process to step S95. On the other hand, in a case where the difference between standardized pixel average water content index Dw1 and standardized pixel average water content index Dw2 exceeds threshold level th, controller 11 determines that the positional deviation occurs, and displays the values of standardized pixel average water content index Dw2 and subsequent standardized pixel average water content index Dw on UI screen 60 by correcting the deviation amount (S94).

After that, controller 11 determines whether to complete the optimum irrigation amount searching control, to complete the cultivation control, or not to complete the cultivation control (S95). In the case where the optimum irrigation amount searching control is not completed, and the cultivation control is not completed, controller 11 returns to the process of step S91. On the other hand, in the case where the optimum irrigation amount searching control is completed, or the cultivation control is completed, controller 11 completes the present operation.

In this way, in plant detection camera 1 of second embodiment, controller 11 as an example of the detection unit detects the positional deviation of the plant. In a case where the positional deviation of the plant is detected, controller 11 calculates coefficient Q (correction coefficient) multiplied by the water content index after positional deviation based on the water content index in before and after the positional deviation. Controller 11 corrects the positional deviation amount by multiplying coefficient Q by the water content index after the positional deviation, and displays the result corrected such that water content index before the positional deviation and the water content index after the positional deviation maintain the continuity on UI screen 60 of monitor 50.

As a result, even in a case where the positional deviation of the leaves occurs, it is possible to maintain the continuity of standardized pixel average water content index Dw in the leaf measured in time series. Accordingly, the measured standardized pixel average water content index Dw data in the leaf can be meaningfully and effectively utilized without being wasted. This makes it possible to efficiently acquire data of standardized pixel average water content index Dw in the leaf in time series, and suppress the increase in the measurement time of standardized pixel average water content index Dw even in a case where the positional deviation occurs on the way.

Modification Example 1 of Second Embodiment

In the second embodiment, the positional deviation of the leaves is determined based on whether or not the difference of standardized pixel average water content index Dw exceeds threshold level th; however, in Modification Example describes a case where the positional deviation of the leaves is physically detected.

Figure 25:
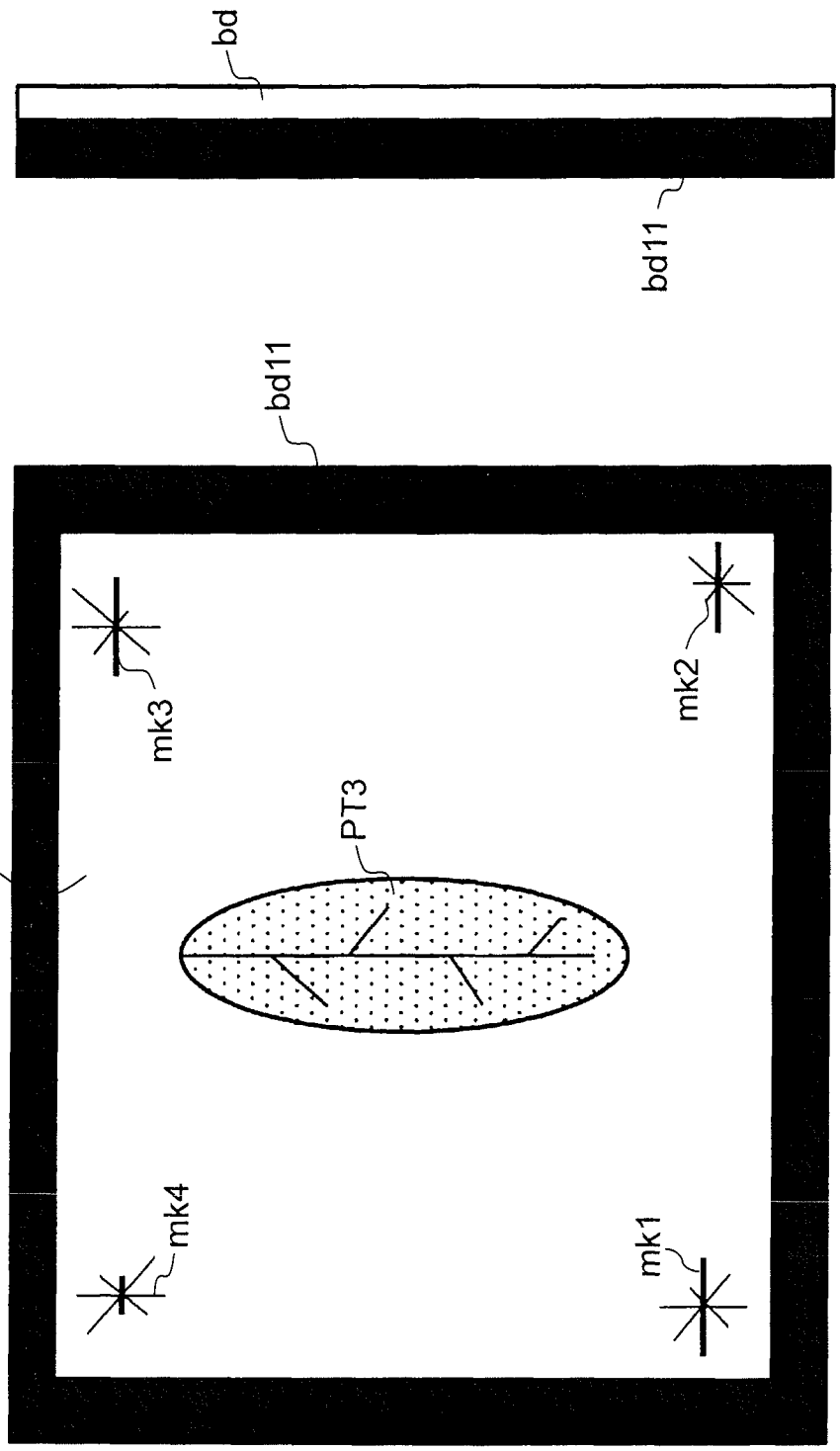
FIG. 25A is a diagram illustrating a white reference substrate used for detecting the positional deviation in Modification Example 1 of the second embodiment, and a front view of the white reference substrate.
FIG. 25B is a diagram illustrating the white reference substrate used for detecting the positional deviation in Modification Example 1 of the second embodiment, and a side view of the white reference substrate as illustrated in FIG. 25A.

FIG. 25A is a diagram illustrating white reference substrate bd used for detecting the positional deviation in Modification Example 1 of the second embodiment, and a front view of white reference substrate bd. FIG. 25B is a diagram illustrating white reference substrate bd used for detecting the positional deviation in Modification Example 1 of the second embodiment, and a side view of white reference substrate bd as illustrated in FIG. 25A.

At the periphery of white reference substrate bd, frame bd 11 of black rectangle having a shape like a picture frame is provided. In addition, marks mk 1 to mk 4 of rice marks are drawn at four corners of the surface (front surface) of white reference substrate bd. Also, leaf PT3 is attached to the center of the surface of white reference substrate bd.

When capturing leaf PT3 attached to white reference substrate bd with plant detection camera 1, parallelism between white reference substrate bd and the finder of plant detection camera 1 is obtained by aligning black frame bd 11 with a finder frame. By capturing white reference substrate bd in this state, each distance between marks mk 1 to mk 4 is compared with the reference distance registered in advance. This reference distance is a distance between marks mk 1 to mk 4 captured in a case where white reference substrate bd is set to be parallel to plant detection camera 1. In a case where each distance between marks mk 1 to mk 4 is shorter than the reference distance, it is determined that white reference substrate bd is tilted to cause the positional deviation.

For example, it is found that as the distance between mark mk 1 and mark mk 4 is shorter than the reference distance, a tilt angle is larger. It is found that as the distance between mark mk 1 and mark mk 2 is shorter than the reference distance, a pan angle is larger.

In this way, it is possible to physically detect positional deviation of the leaves and to measure the positional deviation amount. Furthermore, by registering coefficient Q corresponding to the measured positional deviation amount, when performing the process of multiplying the data of standardized pixel average water content index Dw after the positional deviation, there is no need to use data of standardized pixel average water content index Dw before and after correction. Therefore, the processing load can be reduced.

Modification Example 2 of Second Embodiment

Figure 26:
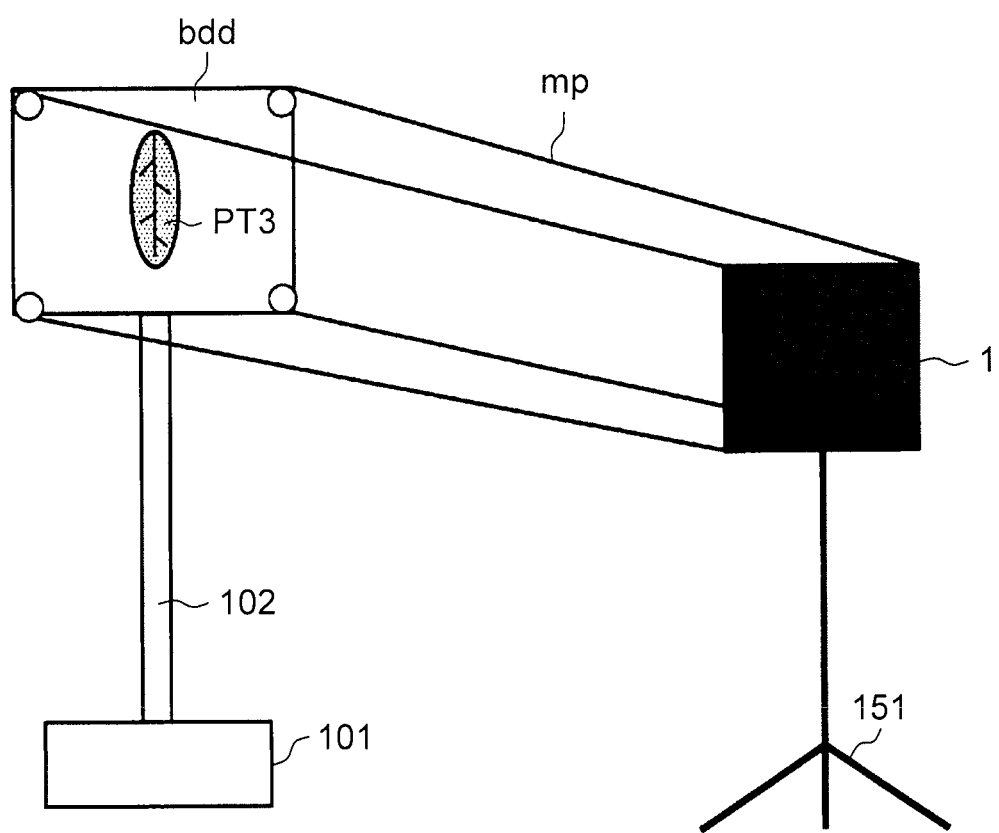
FIG. 26 is a diagram illustrating an example of mechanical disposition of the white reference substrate and the plant detection camera in Modification Example 2 of the second embodiment.

FIG. 26 is a diagram illustrating an example of mechanical disposition of white reference substrate bdd and plant detection camera 1 in Modification Example 2 of the second embodiment. White reference substrate bdd is mounted as a stand on bar 102 standing on base 101. Plant detection camera 1 is fixed to tripod 151. Further, white reference substrate bdd is mechanically connected and fixed to plant detection camera 1 by connecting member mp such as a wire or a bar. In the case where the positional deviation occurs on white reference substrate bdd, the change is transferred to plant detection camera 1 as it is. For example, in the case where large positional deviation occurs, a large change occurs in an image captured by plant detection camera 1.

In a case where the degree of correlation of images captured in time series becomes equal to or smaller than a threshold level, that is, in a case where the similarity between the previous frame image and the current frame image is significantly deteriorated, plant detection camera 1 may determine that the positional deviation occurs on white reference substrate bdd. As a result, it is possible to relatively easily detect the positional deviation of white reference substrate bdd.

In addition, a method for detecting the positional deviation is not limited to the above method. For example, plant detection camera 1 may be equipped with an acceleration sensor for sensing impact. When the positional deviation occurs on white reference substrate bdd, the change of white reference substrate bdd is transferred to plant detection camera 1 via connecting member mp.

In a case where the impact is detected by the acceleration sensor mounted on plant detection camera 1, it may be detected that the positional deviation occurs on white reference substrate bdd.

Although various embodiments are described above while referring to the drawings, needless to say, the present disclosure is not limited to Examples. It is obvious that it is possible for those skilled in the art to conceive of various Modification Examples and Correction Examples within the scope which is set forth in the claims, and therein is naturally understood as belonging to the technical scope of the present disclosure.

Note that, in the above-described first embodiment, as illustrated with reference to FIG. 8 and FIG. 28, plant detection camera 1 calculates reflection intensity ratio Ln $(I_{905}/I_{1550})$ for each reflection position (that is, a position corresponding to a pixel constituting visible light captured image) of the leaves of reference beam LS1 and measuring beam LS2 of the leaf that is an observation target (measurement target), and determines a set of the pixels in which the above calculated value exceeds threshold level Sh (for example, 0.3) as an area corresponding to the pixel of leaf PT3. However, in this determination method, since the area of the pixel regarded as leaf PT 3 is changed with the lapse of time in accordance with the application of water stress, accurate comparison with the initial time becomes difficult, and thereby it may not possible to evaluate the water content over time with reference to the shape of the leaf PT 3 once specified.

Therefore, instead of the method illustrated in FIG. 8, by using the method illustrated in FIG. 29, the area regarded as leaf PT3 at the start (at the initial stage) of measurement of applying the water stress to leaf PT3 of the plant is once and fixedly determined, and the time-transition of the application amount of the water stress (in other words, water content index) thereafter may be evaluated within the determined area.

FIG. 29 is a flow chart illustrating an example of an operation procedure for determining the initial occupation contour (outline) of the leaf as a measurement target. The process as illustrated in FIG. 29 is executed in place of the process as illustrated in FIG. 8 at the same timing as the process as illustrated in FIG. 8, for example.

In FIG. 29, threshold level setter/water content index detector 27a initializes parameter i to 1 (S101), and calculates and acquires reflection intensity ratio Wi (that is, Ln $(I_{905}/I_{1550})$ in pixel Mi) in pixel Mi in i-th frame (S102). Parameter i indicates the number of pixels in the frame, and is in a range of 1 to N.

N indicates the number of pixels constituting one frame image of a leaf. Threshold level setter/water content index detector 27a determines whether or not the reflection intensity ratio Wi calculated in step S102 exceeds threshold level Sh to be regarded as a leaf (S103). Threshold level Sh was described with reference to FIG. 8, and thus the description thereof will not be repeated.

In step S103, in a case where reflection intensity ratio Wi is less than threshold level Sh, the pixel is a pixel that represents a background other than the leaf, and display processor 29 generates monochromatic display data for displaying pixels monochromatically by using the output of threshold level setter/water content index detector 27a (S104).

The generated monochromatic display data is displayed on monitor 50 via display controller 37.

On the other hand, in step S103, in a case where reflection intensity ratio Wi is equal to or greater than threshold level Sh, display processor 29 displays this pixel with a tone color corresponding to reflection intensity ratio Ln $(I_{905}/I_{1550})$ by using the output of threshold level setter/water content index detector 27a (S105). Here, it is possible to display the tone color corresponding to reflection intensity ratio Ln $(I_{905}/I_{1550})$ at n tone (refer to FIG. 27). n is an arbitrary integer.

The tone color was described as above with reference to FIG. 27, and thus the description thereof will not be repeated.

In a case where parameter i has not reached the number of pixels N in the frame (No in S106), threshold level setter/water content index detector 27a increments parameter i (S107), and in accordance with the process of step S102, reflection intensity ratio Wi (that is, Ln $(I_{905}/I_{1550})$ in pixel Mi) in the pixel in the next frame is calculated and acquired (S102).

That is, the processes of step S102 to step S106 are repeated until parameter i has reached the number of pixels N in the frame.

On the other hand, in the case where parameter i has not reached the number of pixels N in the frame (YES in S106), threshold level setter/water content index detector 27a fixedly determine and sets a set of pixels Mi in the frame in which reflection intensity ratio Wi (that is, Ln (I905/I1550)) is equal to or greater than threshold level Sh as the initial occupation contour of the leaf (that is, a contour indicating the range of the observation target portion) at the start of the measurement (that is, at initial stage of the measurement) (S108).

As a result, the user highly accurately compares the time-transition of the water content in the leaf after applying the water stress with reference to the area that is regarded as the leaf at the time when water stress is not applied (that is, the initial stage). Plant detection camera 1 can obtain an appropriate change of the water content in the leaf in time series. Also, since plant detection camera 1 trackingly calculates the water content index for each pixel constituting the set only on the basis of the initially occupied contour as a reference after starting the measurement, it is possible to notify the user that the water content index to the application of the water stress to the leaf is greatly changed by plotting the fact as data on monitor 50 with high accuracy. In addition, display controller 37 outputs the invisible light image of any one of leaves, fruits, stems, and flowers of plants. With this, the user can accurately confirm whether the shape of the plant is correct or not based on the output of the invisible light image. Further, by comparing the visible light image output from display controller 37 with the above-described invisible light image, the user can more accurately confirm whether the shape of the plant is correct or not.

Note that, when viewed from first beam source 13 and second beam source 15, white reference substrate bd (background material) which covers a back surface of leaf PT3 of plant PT is disposed on leaf PT3 of plant PT. With this, with plant detection camera 1, it is possible to eliminate influence due to scattered light (light scattered externally) from the peripheral leaf and accurately measure the water content of leaf PT3 even within the foliage in which multiple leaves grow in abundance on a periphery of leaf PT3 that is the target portion of plant observation.

Further, threshold level setter/water content index detector 27*a* calculates the water content for each reflection position (irradiation position) (that is, for each pixel constituting the invisible light image) in the set of the reflection position which is fixedly determined as a target portion of the plant (in other words, the inside of the set of each pixel constituting the invisible light image of the leaf). Display controller 37 displays the invisible light image in a stepwise and distinguishable manner in accordance with the water content calculated for each irradiation position. As a result, the user can visually recognize the water content of the entire plant as well as the distribution of the water content contained in the plant in time series with reference to the area which is regarded as the once determined leaf of the plant.

Meanwhile, in the description of the cultivation device of the present embodiment described above, the process of non-irrigation such as interrupting irrigation to the plant was performed in order to apply stress (for example, water stress) to the plant (for example, leaf of tomato). However, in the cultivation device of the present embodiment, the method of applying the stress (for example, water stress) to the plant is not limited to the non-irrigation. For example, in order to apply the stress (for example, water stress) to the plant, for example, the cultivation device of the present embodiment may change the electric conductivity of the liquid fertilizer (that is, liquid fertilizer) which is supplied to the plant to be equal to or larger than a predetermined value without using the non-irrigation. In other words, the cultivation device consequently applies water stress equivalent to the non-irrigation to the plant by changing the electric conductivity of the liquid fertilizer so that the electric conductivity of the liquid fertilizer is equal to or larger than a predetermined value. The reason for this is that when the electric conductivity of the liquid fertilizer is changed so as to be equal to or larger than a predetermined value, the root cannot absorb water due to an osmotic pressure relationship (in other words, salt stress is applied), and as a result, the water stress is applied to the plant similar to the case of non-irrigation.

Note that, the aforementioned predetermined value is a known value obtained from the experience of the breeder and is the lower limit value of the electric conductivity of the liquid fertilizer when the salt stress is applied to the plant.

INDUSTRIAL APPLICABILITY

The present disclosure is useful as a device for observing water content, a method for observing water content, and a cultivation device which are capable of quantitatively and time-serially suggesting a change of a water content contained in a plant and accurately capturing the change of the water content from an initial stage with respect to the extent of water stress applied to the plant.

REFERENCE MARKS IN THE DRAWINGS

1 PLANT DETECTION CAMERA
11 CONTROLLER
11*a* TIMING CONTROLLER
13 FIRST BEAM SOURCE
15 SECOND BEAM SOURCE
17 BEAM SCANNER
21, 31 IMAGING OPTICS
23, 33 PHOTO DETECTOR
25 SIGNAL PROCESSOR
25*a* I/V CONVERTER
25*b* AMPLIFIER
25*c* COMPARATOR/PEAK HOLD
27 DETECTION PROCESSOR
27*a* THRESHOLD LEVEL SETTER/WATER CONTENT INDEX DETECTOR
27*b* MEMORY
27*c* DETECTION RESULT FILTER
29 DISPLAY PROCESSOR
35 IMAGE SIGNAL PROCESSOR
37 DISPLAY CONTROLLER
50 MONITOR
60 UI (USER INTERFACE) SCREEN
61 SEARCH IRRIGATION AMOUNT INPUT SCREEN
63 SET AREA
64 INITIAL SETTING BUTTON
66 DEVIATION THRESHOLD LEVEL SETTING BUTTON
67, 68 INPUT BOX
71 IRRIGATION AMOUNT SEARCHING MODE BUTTON
72, 74 DISPLAY BOX
73 WATER STRESS CONTROL (CULTIVATION CONTROL) MODE BUTTON
101 BASE
102 BAR
151 TRIPOD
ARE AREA
BB BASE
bd, bdd WHITE REFERENCE SUBSTRATE
bd1 APERTURE
bd2 HOLE
bd3, bd4, bd5, bd21 SLIT
bd11 FRAME
Bw TARGET RANGE
gh1, gh2 GRAPH
Gm1 SCREEN FOR MONITORING WATER CONTENT IN LEAF
JG DETERMINER
PT3, PT3*t*, PT3*o* LEAF
LS1 REFERENCE BEAM
LS2 MEASURING BEAM
mk1, mk2, mk3, mk4 MARK
mp CONNECTING MEMBER
MT COMMUNICATION TERMINAL
NVSS INVISIBLE LIGHT SENSOR
pf1, pf2, pf3, pf4 WATER STRESS PROFILE
PJ BEAM OUTPUT
TR TIMING SIGNAL FOR BEAM SCANNING
RF BEAM OUTPUT SIGNAL RV0 AMBIENT LIGHT
RV1, RV2 DIFFUSE REFLECTION LIGHT
r1 to r11, r6 to r18, ra, rb, rc ARROW
sc1, sc2, sc3 AREA
sm1, sm2, sm3 PLANT SAMPLE
TW1 WATER POTENTIAL DESCENT PERIOD
TW2 OPTIMUM IRRIGATION AMOUNT SEARCHING PERIOD
TW3 WATER STRESS CONTROL PERIOD
TW4 WATER CONTENT RECOVERY PERIOD
VSC VISIBLE LIGHT CAMERA
WF FERTILIZER OR WATER SUPPLY DEVICE

The invention claimed is:

1. A device for observing water content contained in a plant, the device comprising:
   a first light source which radiates a near infrared laser reference beam of a first wavelength having a characteristic in which light tends not to be absorbed in water while sequentially scanning toward the plant;
   a second light source which radiates a near infrared laser measuring beam of a second wavelength having a characteristic in which light tends to be absorbed in water while sequentially scanning toward the plant;
   an output unit that outputs an invisible light image indicating presence or absence of water contained in the plant;
   a water content calculation unit that repeatedly calculates the water content contained in each pixel area constituting the invisible light image based on reflection light of the near infrared laser reference beam and reflection light of the near infrared laser measuring beam, in a certain measurement period; and
   a controller that displays a time-transition of the water content, which is contained in the pixel area from start to end of a measurement period, calculated by the water content calculation unit on a display unit,
   wherein the controller fixedly determines a set of pixel areas in which the water content calculated by the water content calculation unit exceeds a threshold level at the start of the measurement period, out of all pixel areas constituting the invisible light image, as an observation target portion on the plant.

2. The device for observing water content of claim 1, wherein a background material which covers a back surface of the plant is disposed in the plant as seen from the first light source and second light source.

3. The device for observing water content of claim 2, wherein the water content calculation unit calculates the water content for each pixel area in a set of the pixel areas fixedly determined as a target portion of the plant, and
wherein the output unit displays the invisible light image in a stepwise and distinguishable manner in accordance with the water content calculated for each pixel area by the water content calculation unit.

4. A cultivation device comprising:
the device for observing water content of claim 1; and
a cultivation controller that irrigates the plant with a predetermined amount of water based on a time-transition of water content calculated by a water content calculation unit in a certain period of the measurement periods.

5. A method for observing water content in a device for observing water content contained in a plant, the method comprising:
   radiating a near infrared laser reference beam of a first wavelength having a characteristic in which light tends not to be absorbed in water while sequentially scanning toward a plant, by a first light source;
   radiating a near infrared laser measuring beam of a second wavelength having a characteristic in which light tends to be absorbed in water while sequentially scanning toward the plant, by a second light source;
   outputting an invisible light image indicating presence or absence of water contained in the plant;
   repeatedly calculating the water content contained in each pixel area constituting the invisible light image based on reflection light of the near infrared laser reference beam and reflection light of the near infrared laser measuring beam, in a certain measurement period; and
   displaying a time-transition of the calculated water content contained in the pixel area from start to end of a measurement period on a display unit,
   wherein an observation target portion of the plant is fixedly determined as a set of pixel areas in which the water content calculated at the start of the measurement period exceeds a threshold level, out of all pixel areas constituting the invisible light image.

* * * * *